United States Patent [19]

Einzig

[11] Patent Number: 5,178,153
[45] Date of Patent: Jan. 12, 1993

[54] FLUID FLOW SENSING APPARATUS FOR IN VIVO AND INDUSTRIAL APPLICATIONS EMPLOYING NOVEL DIFFERENTIAL OPTICAL FIBER PRESSURE SENSORS

[76] Inventor: Robert E. Einzig, 360 Herndon Pkwy., Herndon, Va. 22070

[21] Appl. No.: 776,118
[22] PCT Filed: Feb. 25, 1985
[86] PCT No.: PCT/US85/00295
§ 371 Date: Sep. 13, 1985
§ 102(e) Date: Sep. 13, 1985
[87] PCT Pub. No.: WO85/03855
PCT Pub. Date: Sep. 12, 1985

Related U.S. Application Data

[63] Continuation-in-part of Ser. No. 587,464, Mar. 8, 1984.
[51] Int. Cl.[5] .................................................. A61B 5/02
[52] U.S. Cl. ................................... 128/692; 128/673; 128/666; 128/667; 73/861.42; 73/861.52; 356/345; 356/352
[58] Field of Search ............... 128/637, 672, 673, 675, 128/691, 692, 663–667; 73/196, 861.42, 861.52, 861.61, 861.62, 705, 432 L; 356/345, 352

[56] References Cited

U.S. PATENT DOCUMENTS

| | | |
|---|---|---|
| 2,650,497 | 9/1953 | Renwanz ........................... 73/861.67 |
| 2,863,318 | 12/1958 | Schroder . |
| 3,196,680 | 7/1965 | Curran . |
| 3,215,135 | 11/1965 | Franke . |
| 3,249,105 | 5/1966 | Polanyi . |
| 3,552,855 | 1/1971 | Crosswy et al. . |
| 3,686,958 | 8/1972 | Porter et al. . |
| 3,789,667 | 2/1974 | Porter et al. . |
| 3,822,695 | 7/1974 | Takayama . |
| 3,831,588 | 8/1974 | Rindner . |
| 3,866,599 | 2/1975 | Johnson . |
| 4,030,485 | 6/1977 | Warner . |
| 4,201,222 | 5/1980 | Haase . |
| 4,210,029 | 7/1980 | Porter . |
| 4,240,294 | 12/1980 | Gräde .................................. 73/861.52 |
| 4,256,094 | 3/1981 | Kapp et al. ........................ 128/675 |
| 4,321,831 | 3/1982 | Tomlinson et al. . |
| 4,418,981 | 12/1983 | Stowe ................................. 356/345 |
| 4,443,700 | 4/1984 | Macedo et al. ................... 250/227 |
| 4,476,875 | 10/1984 | Nilsson et al. . |
| 4,477,723 | 10/1984 | Carome et al. ................... 324/96 |
| 4,487,206 | 11/1984 | Aagard . |
| 4,508,103 | 4/1985 | Calisi ................................. 128/673 |
| 4,515,430 | 5/1985 | Johnson ............................. 356/345 |
| 4,534,222 | 8/1985 | Finch et al. ....................... 356/345 |
| 4,562,744 | 1/1986 | Hall et al. ......................... 73/861.61 |
| 4,581,530 | 4/1986 | Brogardh et al. ................. 73/705 |
| 4,593,701 | 6/1986 | Kobayashi et al. ............... 128/673 |

FOREIGN PATENT DOCUMENTS

| | | | |
|---|---|---|---|
| 554115 | 11/1921 | France ............................. 78/861.61 |
| 2492562 | 4/1982 | France ............................. 128/672 |
| 8503855 | 9/1985 | World Int. Prop. O. ........ 73/705 |

OTHER PUBLICATIONS

"Fiber-waveguide laser interferometers" by Alekseev et al; Sov. J. Quantum Electron. Sep. 1977; pp. 1161–1162.
"Methods of Flow Measurement" by J. Grey et al; J. of the Amer. Rocket Soc. Jun. 1953; pp. 133–134.
"A Catheter Flow Probe . . . Source Parameters" by Min et al; IEEE Trans. on Biomed. Eng.; vol. BME26 #9; Sep. 1979 pp. 509–512.
"Integrated Signal Conditioning for Silicon Pressure Sensors" by Borky et al; IEEE Trans. on Electron Devices; ED26 #12; Dec. 1979 pp. 906–910.

Primary Examiner—Stephen C. Pellegrino
Assistant Examiner—David Shay
Attorney, Agent, or Firm—Kerkam, Stowell, Kondracki & Clarke

[57] ABSTRACT

An optical fiber fluid flow device is provided for in vivo determination of blood flow in arteries. The device includes a fiber optical fluid pressure measuring device having at least first and second optical fiber sensors which optical fiber sensors are positioned in the blood passage and in a restricted flow area in the blood passage and the two fiber optical pressure fluid sensors are connected to an interferometer associated with an optoelectronic demodulator which has an output signal representing the differential pressure between the two sensed area. The device also has utility in industrial applications.

2 Claims, 14 Drawing Sheets

FLUID FLOW SENSING APPARATUS FOR IN VIVO AND INDUSTRIAL APPLICATIONS EMPLOYING NOVEL DIFFERENTIAL OPTICAL FIBER PRESSURE SENSORS

This application is the U.S. counterpart of application PCT/US 85/00295, filed Feb. 25, 1985, which claims priority of application Ser. No. 587,464 filed Mar. 8, 1984.

INTRODUCTION

This invention is directed to means for measuring fluid flow in arteries and veins of mammals wherein the measurements are provided by differential pressure sensing means positioned in the fluid conduit. With the differential pressure and the knowledge of the cross-sectional area of the conduit, flow rates can be determined. In in vivo flow rate measurements, the diameter of the artery is determined using one of several techniques, such as direct measurement with a probe, two differential pressure measurements, by dye or thermal dilution methods, and by means of x-rays. The invention also has industrial application.

BACKGROUND OF THE PRIOR ART

Means to measure pressure in the human blood stream by a number of techniques are known. However, blood pressure alone fails to provide answers to many questions, such as: whether sufficient volume of blood is flowing to satisfy body needs, the condition of arteries and veins, and the existence of partial blockages that reduce blood flow to critical areas of the body. It is only by determining actual rate and volume of flow that the medical practitioner is provided with greater insight into the actual condition of the circulatory system.

The present invention provides means whereby fluid flow in vivo may be readily determined and in general, the invention comprises one or more fiber optic differential fluid-pressure measuring devices each comprising a first optical fiber sensor and means for positioning the first optical fiber sensor in the flow path at the measurement point. If the devices further consist of several optical fiber sensors, each includes a means for positioning the sensor relative to the measuring position and to each other. In each case, a means for forming a fixed or variable constriction in the flow path of the fluid may be employed. Means are associated with the constriction for positioning the associated optical fiber sensor in the flow path of the fluid at the constriction. The device further includes one or more fiber optic interferometers having either a single leg or a pair of legs with means connecting each of the optical fiber sensors in a leg of an interferometer. Radiant energy is directed into the legs of the interferometers and through each of the sensors; and radiant energy detecting means are connected to the interferometers. The fiber optic probe described may be used in a wide range of veins and arteries (large and small). One specific example chosen for illustration will be the measurement of total cardiac output.

BRIEF DESCRIPTION OF THE DRAWINGS

The invention will be more particularly described in reference to the accompanying drawings wherein.

CHARACTERISTICS OF PULSATILE FLOW

Figure 1:
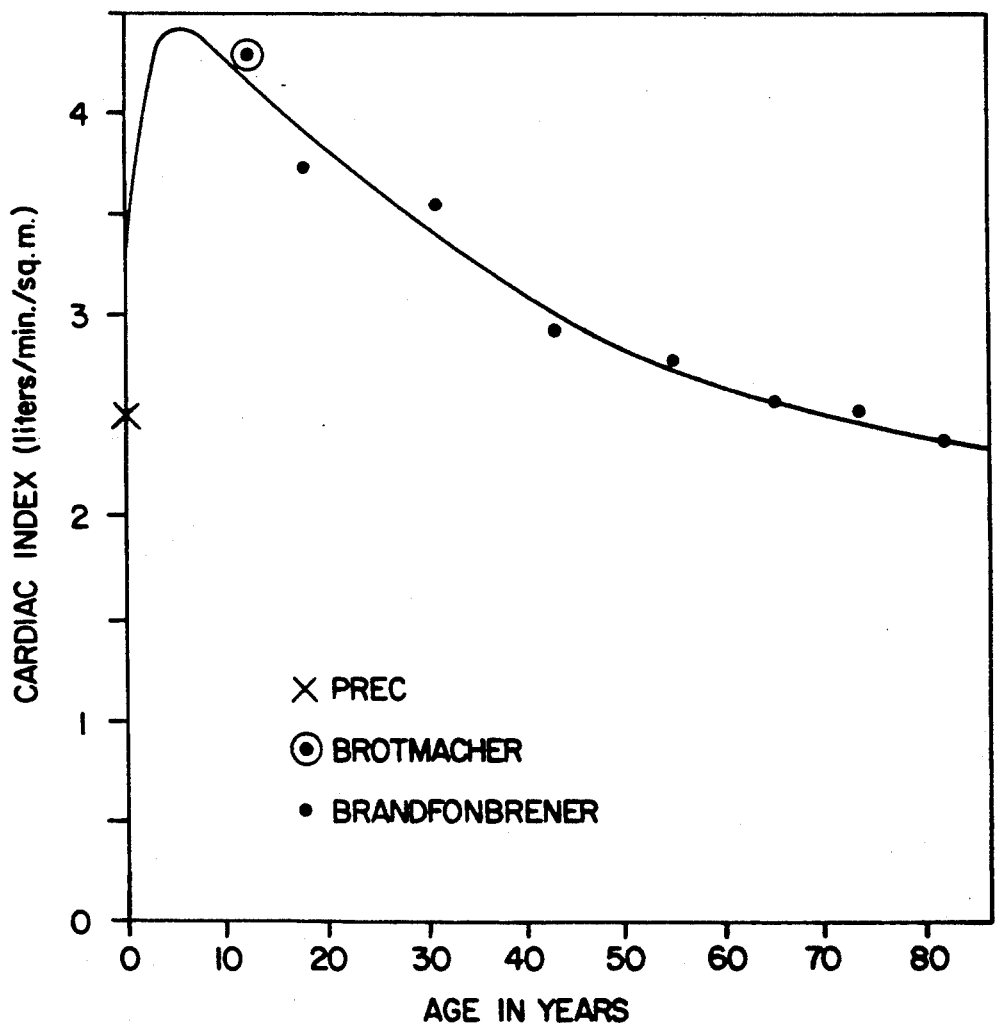
FIG. 1 is a chart illustrating cardiac indices at different ages of a human being.

The cardiovascular system consists of the heart, arteries, capillaries, and veins. All metabolic processes begin and end in this system. These include the exchange of gases in the lungs and in the tissues, the intake of food from the gastrointestinal tract and distribution throughout the body, the transport of nongaseous metabolites from the tissues for elimination in the kidneys, and the dissipation of heat through the lungs and body surface. One of the most important parameters for judging the proper functioning of this system is the quantity of blood transported per unit time (the cardiac output). The output of the ventricles for an adult is approximately 70 ml per pulse and the average pulse rate is 72 beats/min. Thus, the average adult cardiac output is 5040 ml/min. This output may increase significantly upon demand. In the case of athletes during intense exercise, the cardiac output can rise as high as 35 l/min. The specific cardiac output varies with age, sex and body size. The cardiac index is defined as the cardiac output per m² of surface area. For a normal human being weighing 70 kg, the surface area is approximately 1.7 m². The cardiac index is shown in FIG. 1 as a function of age. A reduction of the cardiac index to approximately 1.5 (corresponding to ~2.5 l/min.) will lead to cardiac shock. About 10% of the patients who experience severe acute myocarditis infarction cardiac shock will die.

Figure 2:
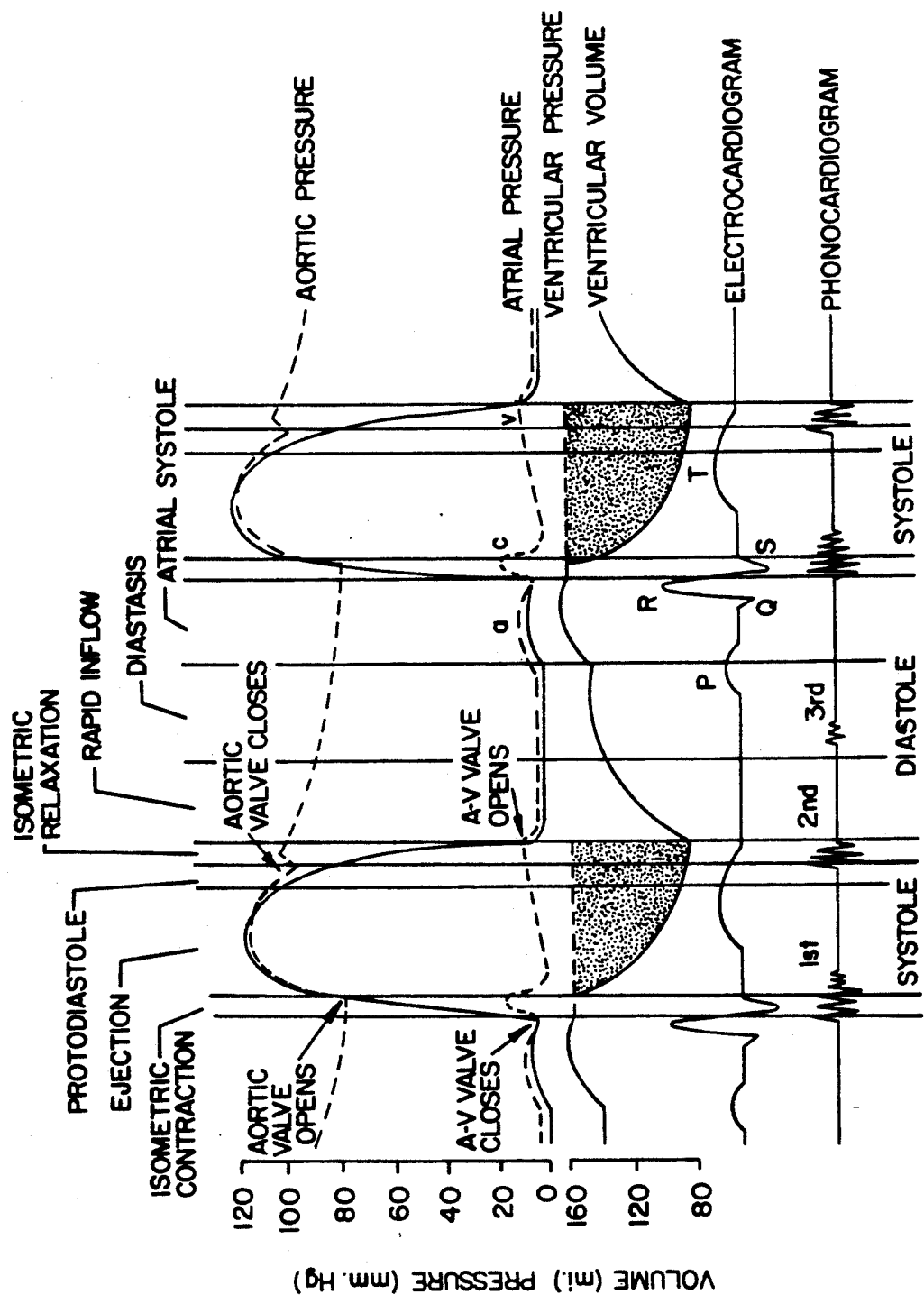
FIG. 2 is a chart illustrating events of a cardiac cycle showing changes in the left arterial pressure, left ventricular pressure, aortic pressure, ventricular volume, the electrocardiogram and the phonocardiogram.

The various events which occur during the cardiac cycle are shown in FIG. 2. The upper three curves illustrate the aortic, atrial, and ventricular pressures, respectively. The fourth curve from the top shows the ventricular volume and the lower two curves are typical traces from an electrocardiogram and a phonocardiogram. Referring to the electrocardiogram, the QRS wave indicates the onset of ventricular contraction. This causes the ventricular pressure to rise and the blood contained to be pumped out as evidenced by the decrease in ventricular volume. The ventricular contraction ends just after the T wave in the electrocardiogram trace. At that time, the ventricle begins to be refilled by the left atrium. Blood is pumped into the main pulmonary artery during the time the ventricle is contracting. The area above the ventricular volume curve during contraction, shown shaded, corresponds to the volume of blood ejected from the ventricle during a single pulse. The derivative of this portion of the ventricular volume curve corresponds to the time rate of change of flow volume. At the point nearest the ventricle, the actual pulse width of the ejected pulse is approximately 1/5 the pulse period, thus, the average pulse height is approximately 25 l/min.

CHARACTERISTICS OF THE ARTERIAL SYSTEM

The total cross-sectional area, blood velocity, and pressure of the main pulmonary artery, aorta, arteries, arterioles, and capillaries are shown in Table I. The velocity of the pressure pulse is approximately ten times the velocity of the blood flow pulse given in this table. As can be seen, the total cross-sectional area of the capillaries is approximately $10^3$ times that of the main pulmonary artery and the aorta and the blood velocity is approximately $10^{-3}$ that in the main pulmonary artery and the aorta. The aorta itself decreases in diameter with distance from the heart. The taper measured by D. J. Patel in large mongrel dogs corresponded to approximately 3% decrease in cross-sectional area per cm. The ascending aorta and main pulmonary artery are relatively elastic. During the pressure pulse Patel et al. have reported that the ascending aorta and pulmonary artery change their diameters by ±6% and ±11%, respectively.

TABLE I

| PART | AREA cm² | VELOCITY cm/sec | PRESSURE mmHg |
|---|---|---|---|
| Main Pulmonary Artery | 6.0 | 30.00 | 20–30 |
| Aorta | 4.5 | 40.00 | 80–120 |
| Arteries | 20.0 | 9.00 | 75–130 |
| Arterioles | 400.0 | 0.45 | 50–90 |
| Capillaries | 4500.0 | 0.04 | 0–30 |

TECHNIQUE FOR FLOW MEASUREMENT

Fluid-flow measurements have a large variety of applications including the measurement of flowing liquids, gases, and slurries for transportation of goods, chemical materials, and vehicle fuel flow. In general, flow sensors consist of a primary element that is in contact with the flowing fluid and a secondary device that measures the action of the fluid stream on the primary element. In the differential pressure technique of the present invention, the primary element is a constriction or section of tube into which is introduced a variation in cross-sectional area. This produces a differential pressure proportional to the flow rate. The secondary element is a differential pressure cell which is the device that measures this differential pressure.

Conventional Techniques for Measuring Cardiac Output

A variety of techniques are presently employed for measuring cardiac output. These include the Fick procedure which involves measuring the ratio of the oxygen absorbed per minute by the lungs to the difference in the oxygen content of the arterial and venous blood. The thermal dilution technique involves injecting a fixed amount of cold solution into the right atrium and measuring the temperature change down stream in a pulmonary artery. The dye dilution method unlike the two above methods, does not involve cardiac catheterization. In this case, a known quantity of dye is injected into a vein and the output of an artery is passed through a photospectrometer which measures the concentration versus time determined. The thermal dilution technique is most often used today. The thermal dilution and an alternate hybrid approach will be discussed in some detail below.

Differential Pressure Technique for Measuring Flow

One method commonly used for determining flow requires the measurement of the differential pressure associated with a change in the cross-sectional area of a flowing liquid. The relevant equation, known as Bernoulli's equation, applies to an incompressible fluid that flows through a tube of varying cross sections. It can be obtained directly from Newton's second law. The Expression can be written in the form $$P_1 + \rho g y_1 + \tfrac{1}{2}\rho V_1^2 = P_2 + \rho g y_2 + \tfrac{1}{2}V_2^2 \quad (1)$$

The subscripts refer to the two points where the measurements are made. P is the absolute pressure in N/m², $\rho$ is the density of the fluid in kg/m³, g is the gravitational constant, y is the elevation at the location of the measurement, and V is the velocity in m/s. Furthermore, from the equation of continuity $$Q = A_1 V_1 \rho = A_2 V_2 \rho \quad (2)$$

one obtains $$V_1 = \frac{A_2}{A_1} V_2 \quad (3)$$

where Q is the quantity of fluid in kg/s and A is the cross-sectional area in m². Assuming Y1=Y2 (in the present application where the orientation will be changing due to movements of the patient, a correction for the elevation may be necessary but for this analysis, will be ignored), and solving for $P_{12}=P_1-P_2$ from Eqs. (1), (2) and (3) yields $$P_{12}=(Q^2/2\rho)(1/A_2^2-1/A_1^2) \qquad (4)$$

A square root relation between Q and $P_{12}$ follows from this expression. The units of $P_{12}$ are n/m² or pa. This can be converted to mm Hg by using the fact that 13.3 pa=0.1 mm Hg. In the present device, the values of Q expected are from 1.0 l/min to 15 l/min ($3.0\times10^{-4}$ kg/s to $4.5\times10^{-3}$ kg/s). In order to attain 0.5% accuracy at the lower limit, it will be necessary to measure cardiac output over 2 orders of magnitude. This requires that the dynamic range of the pressure measurement be 4 orders of magnitude. Conventional catheter pressure measuring devices fail to satisy this requirement by at least 1 order of magnitude. The fiber optic sensors of the invention exhibit the required dynamic range.

Eq. (4) can be solved for Q in terms of the differential pressure and the cross-sectional areas. However, in order to determine the cross-sectional areas, the inside dimensions of the artery must be known. If the artery being measured has a constant cross-sectional area, then the differential pressure can be measured at two adjacent positions and the cross-sectional area of the artery, as well as Q, can be determined.

Two differential pressure measurements $P_{12}$ and $P_{13}$ expressed by equations in the form of Eq. (4) are made. The ratio of these expressions is given by Eq. (5) where Q has been cancelled:

$$P_{12}/P_{13}=(1/A_2^2-1/A_1^2)/1/A_3^2-1/A_1^2) \qquad (5)$$

where $A_1$, $A_2$ and $A_3$ can be expressed in terms of the unknown radius of the artery and the radius of the respective probes in the form $$A_i=\pi r_a^2-\pi\delta_i^2 r_a^2=\pi r_a^2(1-\delta_i^2) \qquad (6)$$

and $r_i=\delta_i r_a$ is the radius of the ith probe. The relation between the values of the various $\delta_i$'s are known for the individual probes, thus letting $$\delta_1=\delta,\ \delta_2=a\delta,\ \delta_3=b\delta \qquad (7)$$

where a and b are known. Substituting Eq. (6) and Eq. (7) into Eq. (5) yields $$P_{12}/P_{13}=[1/(1-a^2\delta^2)^2-1/1-\delta^2)^2]/[1/1-b^2\delta^2)^2-1/(1-\delta^2)^2] \qquad (8)$$

After some algebraic manipulation it can be shown that Eq. (8) becomes $$P_{12}/P_{13}=\frac{[(1-a^4)\delta^2+2(a^2-1)](1-b^2\delta^2)^2]}{[(1-b^4)\delta^2+2(b^2-1)](1-a^2\delta^2)^2]} \qquad (9)$$

which is a cubic equation in $\delta^2$, having at least one real root. Thus, using the measured values of $P_{12}$ and $P_{13}$, $\delta$ can be calculated and used in Eqs. (7) and (6) to obtain the values of $A_1^2$ and $A_2^2$ required in Eq. (4). Thus, with two differential pressure measurements the diameter of and flow through a tube can be continuously monitored.

Alternate techniques of directly measuring the inside dimensions of the artery by an independent technique may be used. These include thermal and dye dilution, ultrasonics, x-rays, etc. In this case only, one differential pressure measurement would be required.

Consideration must be given to measurements made in a tapered region of an artery. In this case, the probes can all be of equal diameter. The differential pressures will be produced as a result of the naturally occurring taper. At the upstream location (i.e., nearest to the ventricle), a variable probe diameter will permit the taper to be measured. This can be accomplished by expanding the diameter of the probe until the value of $P_{12}$ measured between the first two sensing regions is zero and repeating the process until the value of $P_{13}$ between the first and third locations is reduced to zero. The values of Q and the arterial dimensions can then be determined as a function of time from the subsequent measurements of $P_{12}$ and $P_{13}$. In addition to the rate of flow and the dimensions of the vein or artery, the elastic coefficients of the vessel walls can also be determined. This coefficient can be defined by the relation $$E_p=R\Delta P/\Delta R \qquad (10)$$

where R is the mean radius, $\Delta P$ is the pulse pressure, and $\Delta R$ is the change in radius during the cardiac cycle. Values of $E_p$ reported by Patel et al. for various blood vessels are given in Table II.

TABLE II

| Blood Vessel | $E_p$ (g/cm²) |
|---|---|
| Main Pulmonary Artery | 163 |
| Ascending Aorta | 779 |
| Femoral Artery | 4414 |
| Carotoid Artery | 6197 |

The vessels become stiffer (larger $E_p$) with distance from the heart. The value of $E_p$ for the main pulmonary artery is significantly less than that of the ascending aorta except in the case of patients exhibiting pulmonary hypertension. Patel et al. reported on three such patients where the value of $E_p$ corresponding to the main pulmonary artery was observed to be approximately five times the corresponding value given in Table II. Finally the presence and location of stenosis can be determined by the use of such a sensor.

FIBER OPTIC SENSORS

Fiber optic differential pressure sensors have the advantages of no moving parts, applicable to the measurement of flow in most fluids, and well-established performance; however, because of their great sensitivity and large dynamic range, they do not suffer from the disadvantages of conventional differential pressure cells (i.e., limited usable flow range due to the square root relation between flow and differential pressure shown in Eq. (4) and an unrecoverable pressure drop). Thus, both the variation in cross-sectional area introduced by the constriction and the resulting unrecoverable pressure drop may be minimized due to the great sensitivity of fiber optic sensors. Furthermore, the large dynamic range yields a wide usable flow range (>3 orders of magnitude). In addition, fiber optic differential pressure sensors have a number of additional features such as immunity to EMI (electromagnetic interference), ability to operate at high temperatures, small size, high reliability, and low power operation.

A fiber optic pressure sensor consists of at least one optical fiber and a means for enabling the pressure to modulate some property (i.e., phase, intensity, polarization, color, etc.) of the light in the optical fiber. The system consists of a source, one or more photodetectors, a means of demodulating the signal, and various other optical components such as fiber stretchers, fiber deformers, couplers, connectors, mirrors, and means for inserting light from the source into the optical fiber with a minimum of light reflected back into the source. In addition, a means for changing the diameter of the probe and/or to measure the diameter of the veins or arteries may be included.

Phase-Modulated Fiber Optic Sensors

Since the optical frequency is approximately $10^{14}$ Hz, photodetectors are unable to respond and a means for converting the phase modulation to an amplitude modulation is required. This function is provided by the use of an optical interferometer. Three such interferometers (i.e., Mach-Zehnder, Michelson, and Fabry-Perot) will be described below and their advantages and disadvantages compared. All such optical interferometers have some elements in common. In general, they require single-mode: coherent optical sources, optical fiber, couplers and connectors. The light from the source is divided by some means into at least two approximately equal parts. One part being used as the phase reference for the other. A portion of one or both of these parts of light are subjected to the environment being investigated. A section of the optical fiber so subjected is phase sensitized to the parameter being detected. The light is then recombined in such a manner that interference occurs converting the phase-modulated light to intensity-modulated light. The light is then photodetected and the output demodulated.

Mach-Zehnder Interferometer

Figure 3:
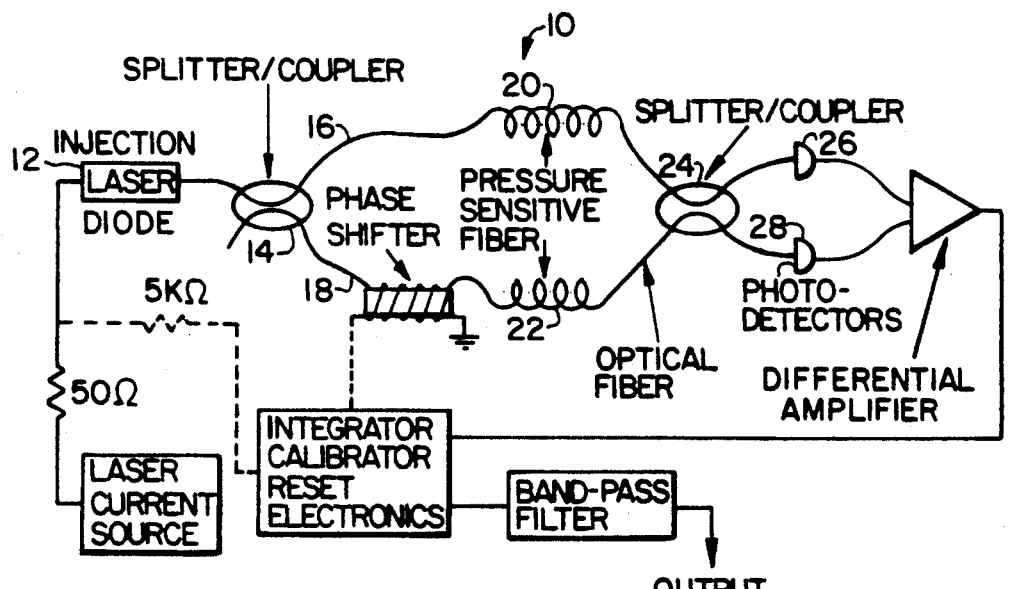
FIG. 3 illustrates diagramatically a Mach-Zehnder interferometer and associated demodulation electronics.

The schematic of a Mach-Zehnder interferometer 10 is shown in FIG. 3. Light from a single-mode laser 12 is divided by the optical coupler/splitter 14 (this device may be either a half-silvered mirror or a fiber-fiber coupler/splitter) between the two arms 16 and 18 of the interferometer 10. Generally, a 50:50 split is preferred in which case a 3 db coupler/splitter is employed. In FIG. 3, a pressure-sensitive region 20 and 22 is shown in each arm of the interferometer.

The pressure sensitive region will be short compared to the overall length of fiber employed in each arm 16 and 18. For the present application, these regions will be spacially separated and the pressure-differential fluctuations between these two regions 20 and 22 measured. If only one arm of the interferometer contains such a pressure sensitive region, then the pressure variations at that location will be measured. The pressure sensitive regions are formed by coating the fibers with a material such as polypropylene in, for example, a one centimeter region for the catheter, and up to several meters for the industrial applications, to be hereinafter designated the "sensitive region" of the sensor. The coating preferaby would be about 100 m in thickness. Thicker coatings may increase sensitivity but are limited by the catheter size. Typically, a catheter whose diameter is 0.3 times the inside diameter of the artery will begin to appreciably decrease the blood flow. Other suitable coatings would be Telfon, nylon and Hytrel. The light in the two arms 16 and 18 of the interferometer 10 are combined by the second optical coupler/splitter 24 and the resulting intensity-modulated light photodetected at 26 and 28. The demodulation/signal-processing circuit performs such functions as common-mode rejection of amplitude fluctuations, integration, filtering, and other functions required in the demodulation of the signal. In and out of band calibration devices may be used and phase-locked-loop feedback techniques may be employed.

Michelson Interferometer

Figure 4:
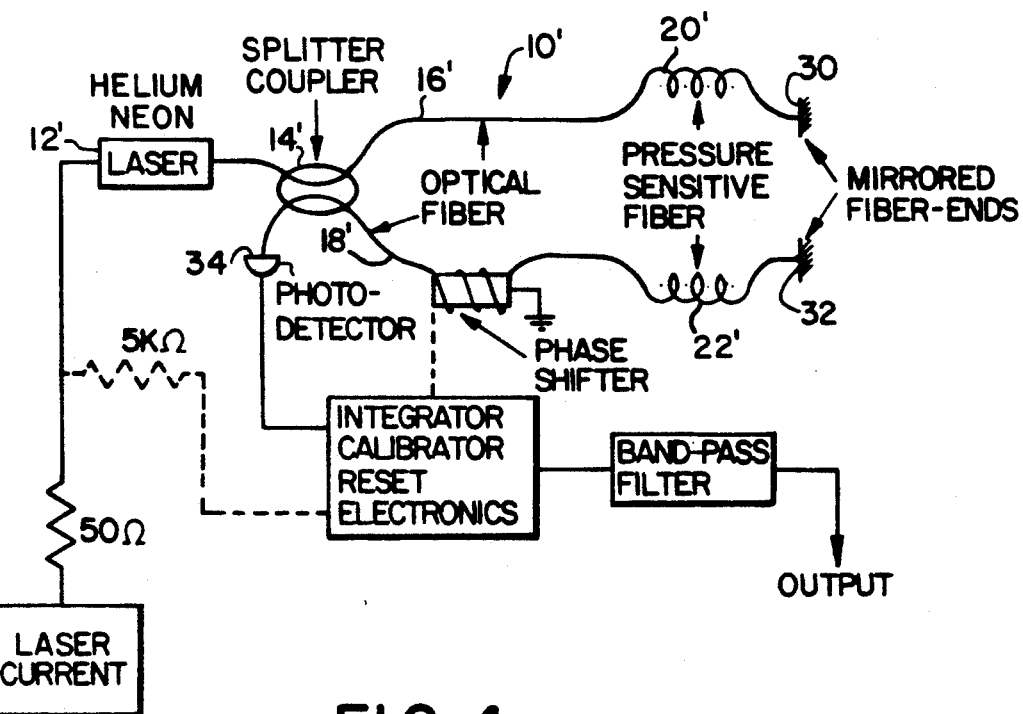
FIG. 4 is a schematic view like FIG. 3 of a Michelson interferometer and associated demodulation electronics.

The schematic of a Michelson interferometer is shown in FIG. 4. Light from the laser 12' is beam split at splitter/coupler 14' between the two arms 16' and 18' of the interferometer 10'. As in the case above, a pressure sensitive region 20' and 22' is provided in both arms 16' and 18' of the interferometer in order to provide the pressure-differential fluctuations between two locations in the flowing medium. The ends 30 and 32 of the two fiber optic arms 16' and 18' are mirrored in order to reflect the light back to the coupler/splitter 14' where phase modulations introduced by the pressure modulations are combined interferometrically producing intensity modulations. A part of the intensity-modulated light is photodetected at detector 34 and the other part travels back to the laser 12'.

Figure 5:
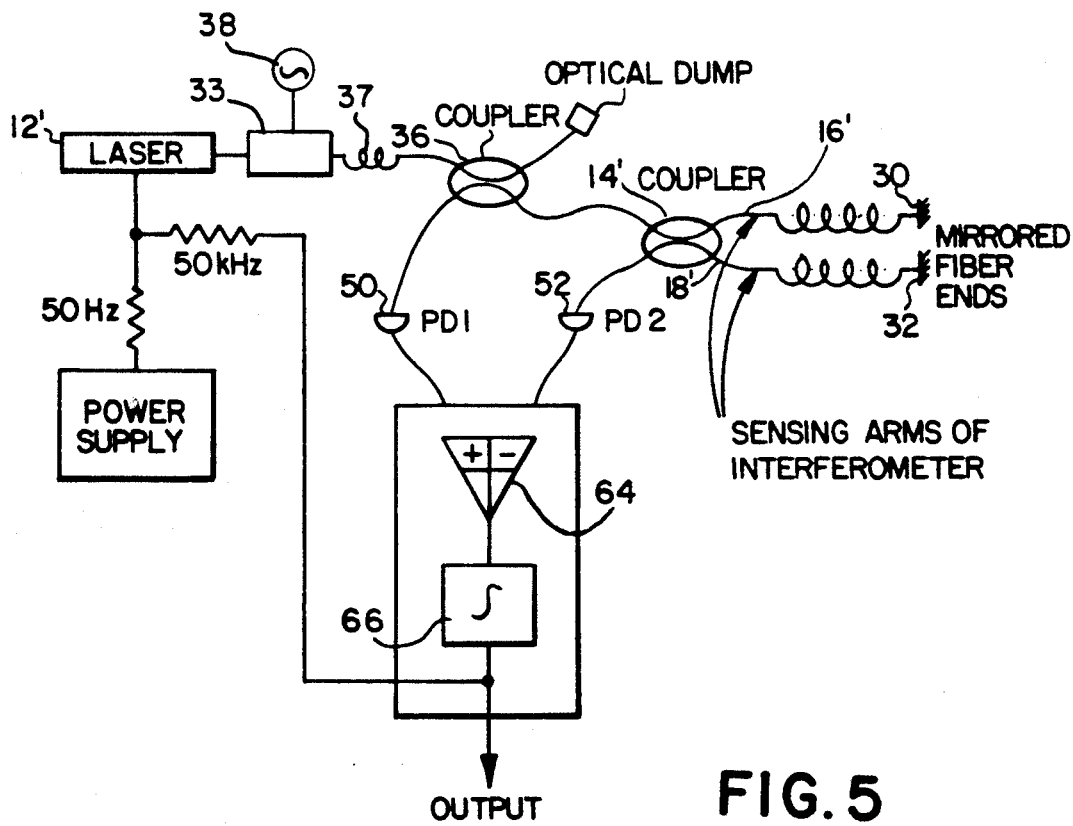
FIG. 5 is a diagramatic showing of a fiber optic Michelson interferometer with phase-locked-loop homodyne detection.

Preferably, some means must be used to minimize the amount of light which travels back into the laser and an alternate schematic is shown in FIG. 5. In this case a second coupler/splitter 36 is provided in order to provide for common-mode rejection of amplitude fluctuations and to reduce the amount of light returned to the laser 12. The portion of the schematic from the second coupler/splitter 36 would be substantially identical to the same portion in FIG. 4. The demodulation/signal-processing circuitry contains similar components and performs similar functions as the electronics described above for the Mach-Zehnder configuration FIG. 4.

Fabry-Perot Interferometer

Figure 6:
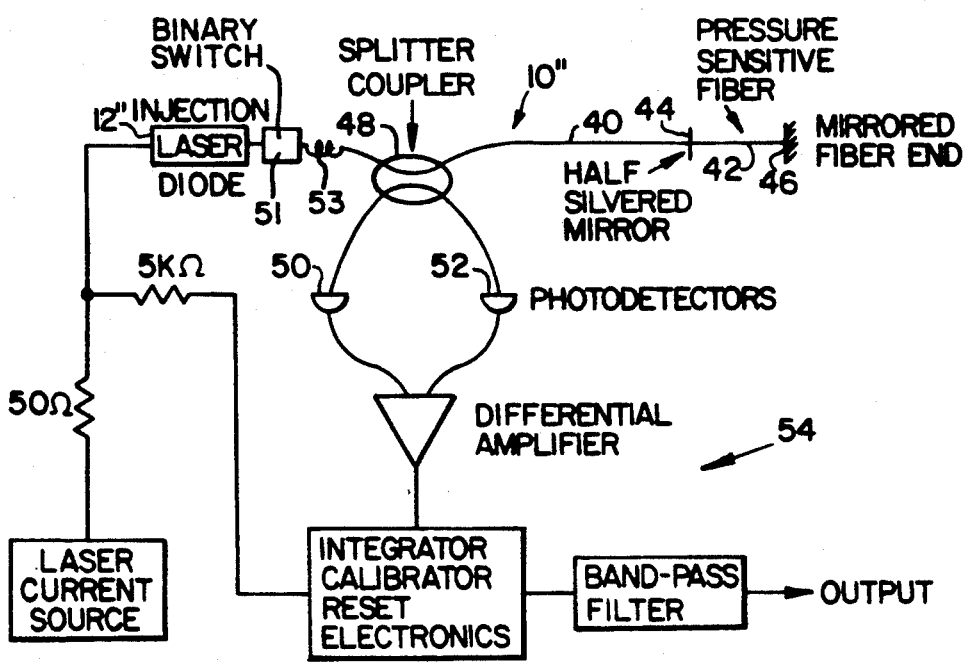
FIG. 6 is a schematic showing of a fiber optic Fabry-Perot interferometer and associated electronics for a pressure measuring device.

The Fabry-Perot interferometer 10'', shown schematically in FIG. 6, differs from the other two in that the two arms of the interferometer are combined in the same optical fiber 40. Thus, only a single pressure may be measured with the configurations shown in FIG. 6. Light from laser 12'' is beam split at the splitter/coupler 48, one part into the fiber 40 and the other portion going to the photodetector 52. At the end of optical fiber 40 is a pressure sensitive region 42 separated from the remainder of the optical fiber by a half-silvered mirror 44. The other end of the pressure-sensitive region is fully mirrored as at 46. Thus, light is divided by the half-silvered mirror, one part being reflected back toward the coupler/splitter 48 and the other part being transmitted into the pressure-sensitive optical-fiber portion 42. The latter part of the light is phase modulated, reflected by the full mirror 46 at the end, and interferometrically recombined at the half-silvered mirror 44 with the part of the light that is not transmitted through the half-silvered mirror. Part of the light in the pressure-sensitive region 42 may be reflected back and forth between the two mirrors 44 and 46 before being transmitted back through the half-silvered mirror 44. Each time the light passes through the phase-sensitive region 42, the phase modulation is increased. The coherence length of the light in the fiber must be greater than twice the length of the pressure-sensitive region 42. The intensity-modulated light propagates back along the fiber to the coupler/splitter 48 where it is divided, one portion going to the photodiode 50 and another portion going toward the laser 12''. The part of this latter portion of light which gets back into the laser must be minimized as shown in FIG. 5. The outputs of the two photodetectors 50 and 52 are combined in the demodulation/signal-processing circuitry 54 which contains similar functions as for the other two interferometer configurations.

In the Fabry-Perot configuration, the pressure fluctuations rather than fluctuations in differential pressure are measured. Thus, in order to measure pressure-differential fluctuations, two such interferometers will be required. Another difference between the Fabry-Perot and the other two interferometers is related to the feedback process. The use of a fiber stretcher to introduce a phase differential is not practical; thus, phase-locked-loop feedback must be applied through the laser source.

Figure 6A:
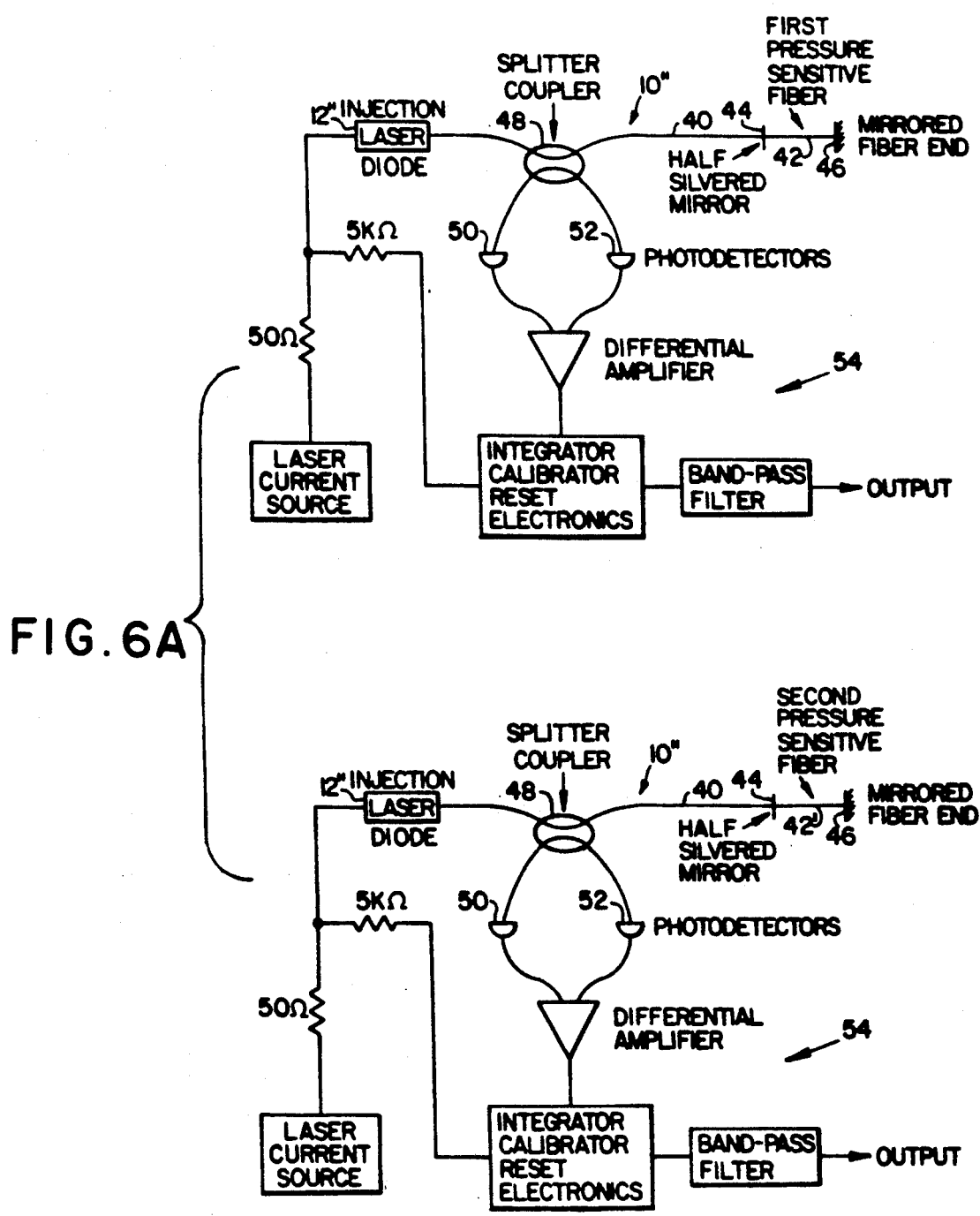
FIG. 6A is a view like FIG. 6 showing a pair of Fabry-Perot interferometers with one sensor in each of the pair of interferometers for measuring differential pressure and measuring fluid flow.

In order to measure differential pressure and/or flow requires two Fabry-Perot interferometers as shown in FIG. 6A with one of the sensors in one of the interferometers and designated 42 and the other of the sensors in the sensing arm of the other interferometer and designated 42'. All of the other components of FIG. 6A are identical with those described in reference to FIG. 6.

Advantages and Disadvantages of the Various Interferometers

The three interferometers considered are compared in Table III. The factors considered are arranged according to their order of importance. The Fabry-Perot has a distinct advantage over the other two with respect to lead sensitivity, ability to obtain pressure directly, and the number of optical fibers and connectors required. The Mach-Zehnder has the advantage of minimizing the problem of optical feedback to the laser; however, it fares worse with respect to lead sensitivity and the number of optical fibers and connectors required.

Detection Circuitry

A schematic of typical detection circuitry is shown in FIG. 5 for the case of feedback to the laser applied to the Michelson interferometer. Schematics required for the Mach-Zehnder and the Fabry-Perot interferometers are similar.

Figure 7A:
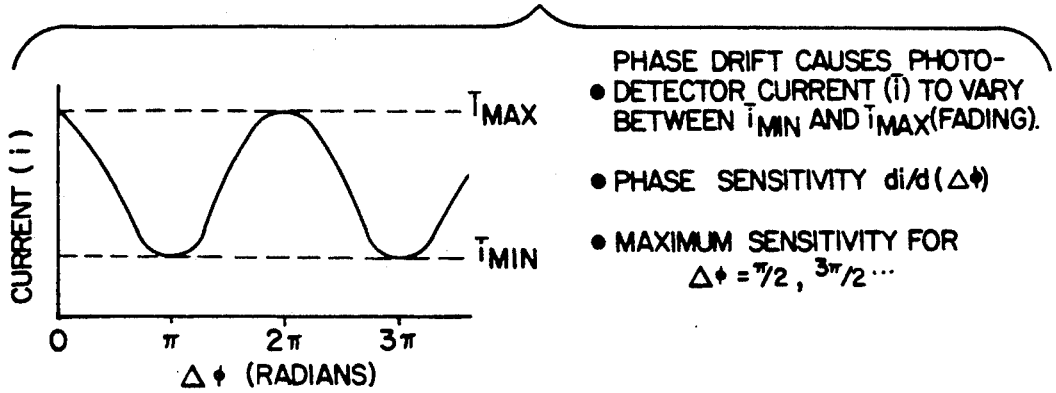
FIGS. 7A and 7B graphically illustrate photo detector output current and its derivative resulting from light wave phase-change fiber optic sensor output.

If the outputs of the two arms 16' and 18' of the interferometer are initially in phase, they will interfere constructively when recombined. If the difference in phase, $\Delta\Phi$, between the two arms of the interferometer increases because of a pressure fluctuation, the amplitude of the output signal from both photodetectors 50 and 52 decreases, reaching a minimum when $\Delta\Phi=\lambda/2$ (i.e., $\pi$ radians). If the value of $\Delta\Phi$ continues to increase, the output amplitude will increase, returning to its maximum value when $\Delta\Phi$ becomes $2\pi$. The electrical current out of one of the photodetectors 50 or 52 caused by the optical signal is shown in FIG. 7A. The outputs of the two photodetectors 50 and 52 are combined in a differential amplifier 64 FIG. 5. Since the amplitude modulations of the current from the two photodetectors are 180° out of phase, combination in the differential amplifier rejects common-mode amplitude fluctuations.

By carefully matching of the lengths of fiber in the interferometer arms 16' and 18', laser phase noise can be reduced by five to six orders of magnitude. In this manner, values of $\Delta\Phi$ of $10^{-5}$ radians and below can be detected at low frequency (i.e., $\sim 1$ Hz).

Figure 7B:
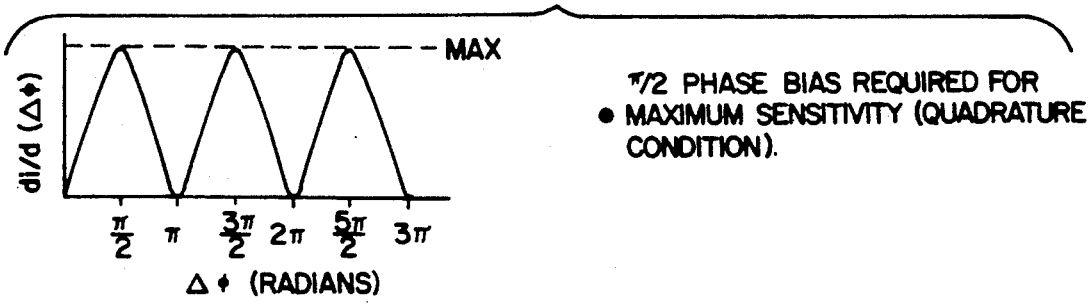
Figure 9:
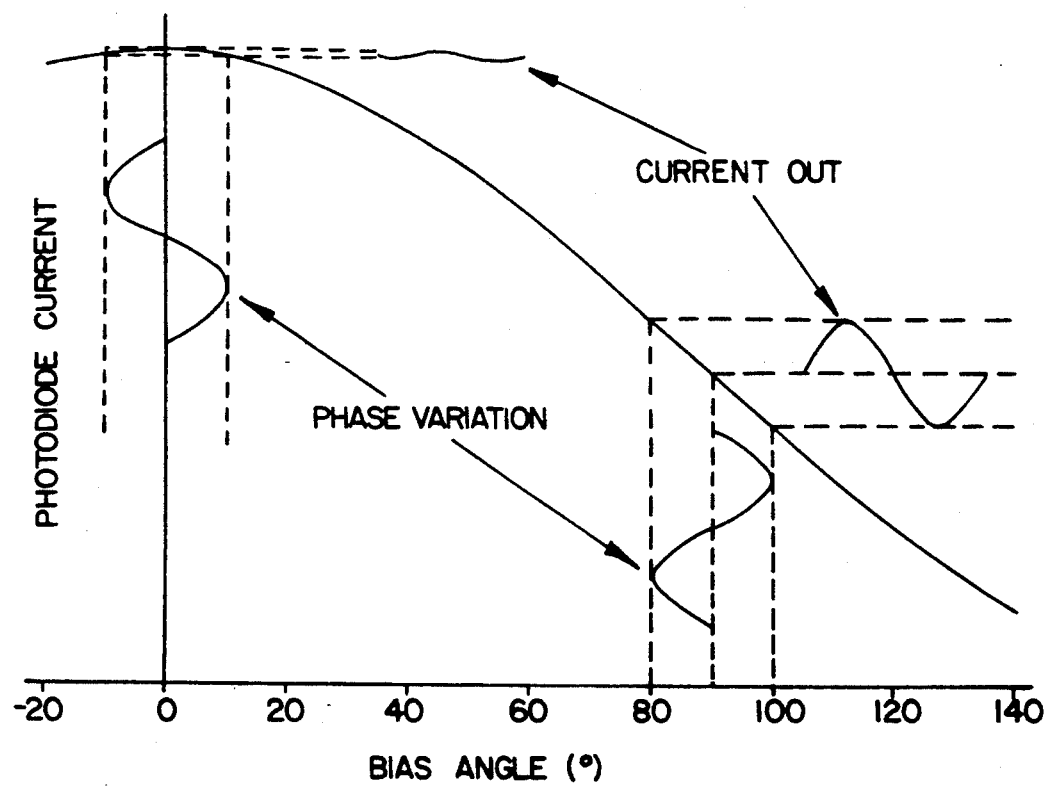
FIG. 9 graphically illustrates the sensitivity of fiber optic homodyne sensor at 0° and 90° bias angle.

The feedback circuit also ensures that the interferometer is operated in its most sensitive mode. Any large amplitude drift (change) greatly increases the difficulty of measuring small changes. The signal to be considered will appear as a small amplitude perturbation on the photodetector current, as shown in FIG. 9. The sensitivity to phase changes varies as the slope of the photodetector curve. Thus, the curve of FIG. 7B, obtained by taking the derivative of the photodetector output with respect to $\Phi$, is the phase sensitivity for small amplitude changes. The maximum sensitivity occurs for odd multiples of $\pi/2$, while zero sensitivity occurs for even multiples of $\pi/2$. This is shown in FIG. 9. Here the photodiode current is plotted against the bias (phase) angle. In order to demonstrate the sensitivity, a cw (sinusoidal) signal of amplitude 10 (electrical degrees) is shown superimposed on a bias (quiescent or operating value of the relative phase) point at 0° and at 90°. The amplitude of the resulting output current is obtained by projecting the phase oscillation (input signal) upward onto the solid curve graphically and plotting the resulting output current along a horizontal line, as is normally done graphically with any transfer function. At 90° bias, the resulting current is large and of the same frequency as the input signal. At 0° bias, however, the amplitude of the photodetector current is small and exhibits a frequency that is twice the excitation frequency because the oscillation extends on both sides of the maximum. Thus, consider such a signal initially at the 90° bias. The magnitude of the input signal shown in FIG. 9, beginning at the 90° bias point, if the bias point begins to drift toward 0° (e.g., as the result of the return to equilibrium following a temperature change) the amplitude of the photodetector current decreases, and at less that 10° bias, a second harmonic appears. The photodetector current amplitude becomes a minimum at a 0° bias, at which point the fundamental component will be zero with only a small second harmonic remaining. This process is referred to as "fading". The 90° bias condition is known as "quadrature". This mode of detection is called "homodyne detection".

Figure 8:
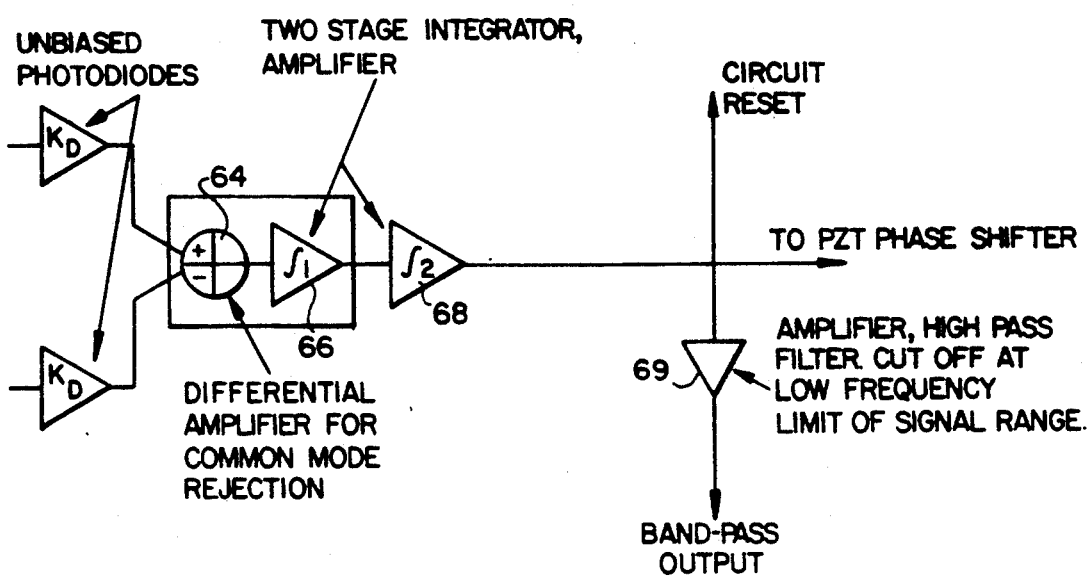
FIG. 8 schematically illustrates a phase-locked-loop homodyne detection circuit.

Returning to FIGS. 5 and 8, the output of the differential amplifier 64 is integrated to eliminate drift and feedback to the laser power supply introduces sufficient frequency shift to compensate for the phase shift. The result of either this approach or feedback fiber stretchers located in the interferometer (not shown)is to lock the relative phase at the point of maximum sensitivity. A schematic of a circuit to accomplish this is shown in FIG. 8.

TABLE III

|  | MACH-ZEHNDER | MICHELSON | FABRY-PEROT |
| --- | --- | --- | --- |
| Fiber Lead sensitivity and numbers | Fiber lead sensitivity only partially cancelled and is, thus, a significant problem. | Fiber lead sensitivity only partially cancelled and is, thus, a significant problem. | Fiber lead sensitivity reduced essentialy to zero. |
|  | Requires 4 leads per differential-pressure sensor. | Requires 2 leads per differential-pressure sensor. | Requires 2 leads for the first differential-pressure sensor but only one |

TABLE III-continued

| | MACH-ZEHNDER | MICHELSON | FABRY-PEROT |
|---|---|---|---|
| | | | additional lead for each additional differential pressure sensor. |
| Optical feedback to laser | Optical feedback problems minimized. | Optical feedback problems significant. | Optical feedback problems significant. |
| Sensitivity and dynamic range | Excellent | Excellent | Excellent |
| Pressure Measurement | Requires a separate sensor. | Requires a separate sensor. | May be obtained directly. |
| Number of connectors required to measure oen pressure differential, two pressure-differentials, and also to measure pressure | 4, 8, or 10 connectors. | 2, 4, or 6 connectors | 2 or 3 connectors. |
| Optical source, detectors, and electronics | Single-mode laser, PIN detector, demodulation electronics | similar to Mach-Zehnder | similar to Mach-Zehnder |
| Feedback | To laser or fiber stretcher | To laser or fiber strecher | To laser |

Two photodetectors are shown in FIGS. 5 and 8. The photodetectors are operated in an unbiased condition in order to eliminate dark current noise. Their outputs are combined in the differential amplifier 64 that provides common-mode rejection as well as amplification. This is followed by one or more stages of integration at 66 and 68 and, possibly, additional amplification. These two integrator amplifiers 66 and 68 pass all signals from DC up to the highest frequency of interest. The output of the two-stage integrator amplifier is used to phase lock the arms of the interferometer. The effect is to produce a phase change in the interferometer arms equal to that caused by the signal being detected. In addition, the interferometer is maintained in quadrature, i.e., is phase locked. If the phase were exactly locked, there would be no output signals from the interferometer. However, there must be an error signal at the photodetectors in order to have a feedback signal. The feedback circuit thus amplifies the error signal from the interferometer back to the level of the signal being detected. If the system is initially at a bias (operation or quiescent) point away from quadrature, there is insufficient output from the interferometer for the compensation circuit and the system will tend to drift toward an increasing error signal and, therefore, toward quadrature. In addition to establishing quadrature, the feedback circuit increases the dynamic range to as much as eight orders of magnitude.

The signal out of the compensating circuit is also fed through a filter 69 that passes the frequency band of interest. This constitutes the output of the interferometeric sensor.

In the feedback schematic shown in FIG. 8, operational amplifiers (OPAMPS) are used and combined metal oxide semiconductor (CMOS) components are used in the reset circuit. The levels of voltage that can be applied by these circuits to the phase shifter are on the order of ±10 volts. The reset circuit tracks the voltage applied to the laser (or phase shifter) and if the limit of the circuit begins to be reached, the phase shifter is rapidly reset to the initial condition and the tracking process begins again. The phase change associated with a large-amplitude, slow drift is compensated for by a number of saw-toothed-like small amplitude phase changes. Care must be taken to minimize the noise during the reset process. In a thermally stable environment, it is common for reset not to occur.

Lead Sensitivity

For the present application, the pressure sensitive regions of the fibers are shorter by several orders of magnitude than the length of fiber in the leads. Since optical fibers tend to be sensitive to both pressure and temperature changes, a significant amount of unwanted noise is detected. For the Mach-Zehnder and Michelson interferometers, configuring the leads together tends to subject both arms of the interferometer to the same influences and, therefore, partly cancels the effect of these influences. The degree of cancellation by this means is approximately a factor of 10. The magnitude of the remaining unwanted noise associated with leads, therefore, may still significantly exceed the signal being measured. In the case of the flow catheter, that portion of the unwanted signal introduced due to the pressure pulse associated with ventricular contraction exhibits characteristics similar to the signal being detected. For the Fabry-Perot, a single lead is employed; thus, the portion of light which reaches the pressure sensitivity section of fiber also travels the identical path traversed by the reference light, therefore, the cancellation of unwanted signal is essentially completed.

Optical Feedback to Diode Lasers

The effects of optical feedback into injection diode lasers include satellite modes, mode hopping, and multi-mode operation. The effect of satellite modes can be eliminated by matching the lengths of fiber in the two arms of the interferometer. Mode hopping and multi-mode operation can be eliminated only by reducing reflections back into the interferometer to 0.1% or less. In the case of the Mach-Zehnder interferometer, by exercising care in making splices, cutting fiber ends at an angle to eliminate back reflections, and employing index matching, reflections can be reduced below 0.1%.

These methods are insufficient for the Michelson and Fabry-Perot interferometers where a significant part of the light into the interferometer is reflected by the mirrored fiber ends and retraces its path back to the laser.

Figure 10:
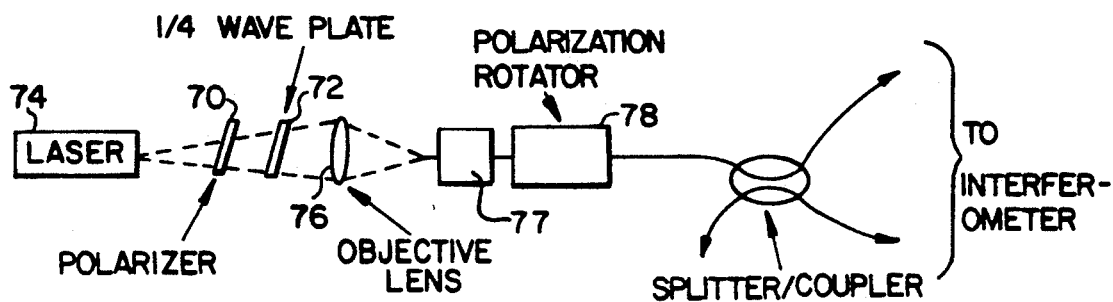
FIG. 10 schematically illustrates a technique for reducing optical feedback in a laser-supplied interferometer.

A significant reduction in light back out of the interferometer into the laser can be achieved by the technique shown in FIG. 10. In this case a polarizer 70 and a ¼ wave plate 72 are located between the laser 74 and the objective lense 76. Each of these devices is oriented at a slight angle ($\sim 12°$) in order to eliminate back reflections. In addition, a fiber optic polarization rotator 78, located in the input fiber 80, allows a twist to be applied to the fiber, thus rotating the direction of polarization. The output of the single-mode injection laser diode 74 is approximately 95% polarized; therefore, by properly orienting the polarization rotator 78, the output can be polarized with very little optical loss. The ¼ wave plate 72 rotates the direction of polarization by 45°. Light reflected off of surfaces, such as the objective lense 76, and passing back through the ¼ wave plate have their direction of polarization rotated by an additional 45°. The net result is a 90° rotation in the direction of polarization relative to the orientation of the polarizer. Such back reflected light is blocked by the polarizer. The fiber optic polarization rotator 78 is adjusted such that the direction of polarization along which that component of light is oriented, exits from the fiber with an orientation, relative to the ¼ wave plate and polarizer, preventing that fraction of light from reentering the laser. Using this arrangement, satisfactory operation can be achieved for either the Michelson or Fabry-Perot configurations. The use of cleaved-cavity injection laser diode may significantly improve the results achieved with this approach. This is due to the fact that these lasers are much less suceptible to mode hopping.

Referring to FIG. 5, a more effective technique involves the use of an acoustooptic modulator 33 and an added length of fiber 37 in the input to the interferometer such that the round trip time through the interferometer corresponds to ½ the period of the acoustooptic modulator. The output of the laser 12' is collimated and passed through the acoustooptic modulator (Bragg cell). The Bragg shifted optical beam is collected and focused into the optical fiber. The Bragg cell is modulated by oscillator 38 with a square wave whose period is twice the round trip travel time through the interferometer. Thus, during the time it takes the pulse of light to pass through the interferometer, be reflected at the mirrored fiber ends 30 and 32, and retrace its path to the Bragg cell, the Bragg cell has been turned off preventing the light from reaching the laser. Light travels with a velocity of $\sim 5$ ns/m in optical fiber, thus, the round trip time through 100 m of optical fiber is 1 µs. This requires that the Bragg cell modulation frequency be 500 KHz. Alternately, 50 m of fiber and a 1 MHz modulation frequency will suffice. A disadvantage of this technique is the associated increased optical alignment problems.

An alternate arrangement involves turning the laser on and off. A length of fiber 37 is again employed as a delay. The length of fiber and the modulation frequency are adjusted such that the back reflected light reenters the laser during the time it is shut off. In this case, the optical fiber can be directly pigtailed to the laser.

Referring to FIG. 10, still another arrangement involves placing an electro optic modulator 77 between the laser and the input fiber to cut the light on and off without modulating the laser itself. The electro optic modulator can be constructed on an intergrated optic chip or can be in the form of a bulk optical component. Another form of electro optic device is a binary switch 51 (see FIG. 6). When the switch is on the incident beam from the laser is introduced to the input waveguide and coupled into the interferometer waveguide which is connected to the interferometer. A length of fiber 53 is again provided as a delay. The light reflected from mirrored ends 30 and 32 of FIG. 6 arrives back at the binary switch when it is off. This returning light is not coupled to the input waveguide therefore missing the laser.

Interferometric Sensor Probes

Two techniques for the fabrication of probes that exhibit sufficient sensitivity for the present application will be described below. The required sensitivity calls for a minimum detectable pressure of 0.1 mm Hg (13.3 N/m$^2$) and a dynamic range of 4 orders of magnitude. Furthermore, the probe size must be compatible with catheter dimensions. A probe with a diameter and length of approximately <5 mm and 1 cm, respectively, would be satisfactory. The frequency range of interest for medical applications is from 0.5 Hz to 500 Hz. For other applications, it will be higher. Techniques for fabricating two types of probes which meet these requirements will be described below.

Transduction Mechanism Due To Pressure Induced Length Changes

The transduction mechanism by which hydrostatic pressure induced length changes produces a phase change in the optical path length is discussed below. The phase $\Phi$ can be expressed in terms of the refractive index n, the fiber length, L, and the wave number, k, by the equation $$\Phi = knL \qquad (11)$$

where $k = 2\pi/\lambda_0$ and $\lambda_0$ is the wavelength of light in vacuum. Changes in k, n, and L result in changes in $\Phi$. The corresponding expression relating these changes is $$\Delta\Phi = k\Delta(nL) = knL(\Delta n/n + \Delta L/L) \qquad (12)$$

where $\Delta L/L$ is the axial strain, $S_{11}$, and $\Delta n$ is given by $$\Delta n = (n^3/2)[(P_{11}+P_{12})S_{12}+P_{12}S_{11}] \qquad (13)$$

where $P_{11}$ and $P_{12}$ are the Pockel's coefficients and $S_{12}$ is the radial strain. For changes occurring at constant volume $S_{12} = -\frac{1}{2}S_{11}$. This expression assumes a value of 0.5 for Poissons ratio. This assumption is valid for the jacket and mandrel materials which will be used since their Poissons ratios approach 0.5 (e.g., in Hytrel$^c$ the value of the Poissons ratio is 0.483). Combining Eqs. (12) and (13) and expressing $S_{12}$ in terms of $S_{11}$ yields $$\Delta\Phi = knL[1+n^2(P_{11}-P_{12})/4]S_{11} \qquad (14)$$

The strain $S_{11}$ can be applied in a variety of ways, two of which are the use of specialized materials as the fiber jacket or as a mandrel on which the fiber is wound. The former approach will be used for the present application. In fused silica, $P_{11}$ 0.12, $P_{12}=0.27$, and $n=1.46$. Substituting into Eq. (14) becomes $$\Delta\Phi = 0.92kLnS_{11} \qquad (15)$$

The $\Delta n/n$ term in Eq. (12) affects the value of $\Delta\Phi$ by only 8% (i.e., if $\Delta n/n$ were neglected in Eq. (12), then $\Delta\Phi = knLS_{11}$ would result). The value of $S_{11}$ depends upon the configuration of the optical fiber and the manner in which the stresses are applied. If the fiber has a thick jacket, the value of $S_{11}$ will be dominated by the jacket material. For an isotropic material subjected to hydrostatic pressure, $$\Delta L/L = \Delta V/3V \approx (\tfrac{1}{3}V)(\delta V/\delta P)\Delta P \tag{16}$$

where the volume, P is the hydrostatic pressure, and $(1/V)(\delta V/\delta P)$ is the compressibility, K. Thus, Eq. (16) becomes $$\Delta\Phi = 0.31\, kLnK\Delta P \tag{17}$$

This expression is valid for the thick coating case where the pressure sensitivity is determined by the fiber jacket alone. For thinner jackets, $S_{11}$ is not a function of the jacket compressibility alone. For jackets of finite thickness, to first approximation, the value of $S_{11}$ is goverened by an effective Young's modulus, defined as the cross-section area average of the Young's modulus of the glass and of the jacket material. The maximum value of $\Delta\Phi$ will not exceed the value indicated by Eq. (17). For materials with a large Young's modulus, thick-jacket behavior can be realized with relatively thin jackets. The ideal jacket material will, therefore, have large compressibility and large Young's modulus. Some materials that meet these requirements are Teflon, polypropylene, nylon, and Hytrel. Solving Eq. (17) for the minimum detectable differential pressure, $\Delta P$, in terms of the minimum detectable phase change, $\Delta\Phi_{min}$, yields $$\Delta P_{min} = \Delta\Phi_{min}/L(0.31\, nkK) \tag{18}$$

Letting $\lambda_0 = 0.82 \times 10^{-6}$ m $K = 2.67 \times 10^{-10}$ m$^2$/n (Hytrel), and $n = 1.46$ in Eq. (18), results in $$\Delta P_{min} = 1.08 \times 10^3 \Delta\Phi_{min}/L(m) \tag{19}$$

For $L = 0.01$ m and $\Delta\Phi_{min} = 10^{-4}$ rad, $\Delta P_{min} = 10.8$ N/m$^2$ = 10.8 pa, which satisfies the sensitivity requirement indicated above. The value of $\Delta P_{min}$ is defined as $S/N = 1$ measured in a 1-Hz band. The dynamic range achievable with these probes is 6 orders of magnitude. The results are relatively flat over the frequency range of interest.

Transduction Mechanism Due To Pressure Induced Bending

When an optical fiber is bent, the side of the fiber furthest from the center of curvature is placed in tension and the side of the fiber nearest the center of curvature is placed into compression. The stress at intermediate points varies linearly between these limitations. Thus, points along the axis of the fiber are essentially unstressed. For an optical fiber with a 125 m cladding diameter bent along a curve having a 50 cm radius, the difference in length between the two sides of a 1 m long fiber is 125 m (or 1.25 m/cm). For an injection diode laser with a 0.82 m wavelength, this corresponds to approximately 10 rad/cm phase change. If the core were concentrically located, the strain would nevertheless average to zero; however, in general, some degree of asymmetry can be expected. If the core of 1 cm length of such a bent fiber is located as little as 1 m from the center, the resulting phase change associated with this bending radius will be 0.15 rad. Applicant has fabricated probes in such a manner as to take advantage of this effect. A bare fiber was configured in a length of loose fitting capilliary tubing. The fiber, unsupported at the fully-mirrored end, was allowed to assume a natural curvature. Using a hypodermic needle, the capilliary was then filled with silicone rubber. The length of fiber between the $\tfrac{1}{2}$ mirrored and the fully-mirrored ends was 2 cm. The total round trip path length of 4 cm. The value of $P_{min}$ measured with this probe was less than 1 n/m$^2$ ($<0.01$ mmHg). The dynamic range achievable with these probes is 6 orders of magnitude over a frequency range of 0.5 Hz to 500 Hz.

CONTINUOUSLY MEASURING CARDIAC OUTPUT

Two approaches for monitoring cardiac output are described. They differ with regard to the measurements required as well as the data they will provide.

The most comprehensive method makes use of two independent $\Delta P$, pressure differential, measurements and eliminates the cross-sectional area of the artery as a variable as this area can be calculated as described herein. This combined with a pressure measurement gives the elasticity of the vein or artery (see Table II). In addition, with a variable constriction built into the catheter, the taper of a vein or artery can be measured.

The second method makes use of a single differential pressure measurement and a separate initial measurement for determining flow rate. In this case, the cross sectional area of the vessel need not be known. A variety of currently used methods would suffice.

a. Thermal dilution
  b. Dye dilution
  c. Etc.

In the description which follows, the thermal dilution technique will be considered. Once the value of $\Delta P$ has been calibrated with an independent flow, measurement (e.g., using thermal dilution), it then is only necessary to monitor the value of $\Delta P$ continuously and use it as a measure of flow rate and volume. This measurement will be independent of area or taper of the artery.

Continuous Monitoring of Cardiac Output Using Thermal Dilution for Calibration The major factor determining the quantity of blood pumped by the heart in a given time is the quantity of blood which flows from the veins into the heart during the same time. The blood from the veins is known as the venous return. The perpheral tissue of the body controls its own blood flow. The blood which passes through the peripheral tissue returns by way of the veins to the right atrium. The intrinsic ability of the heart to adapt to widely varying blood input from moment to moment is known as the Frank-Starling law of the heart which may be simply stated: within physiologic limits, the heart pumps all the blood that comes to it without allowing excessive daming of the blood in the veins.

The physiological basis of the Frank-Starling law can be explained as follows:

When an excess (deficit) amount of blood enters the heart chambers, the heart muscles expand further (less). The force of contraction of striated muscles (such as the heart or skeletal muscle) is proportional to their extension (so long as that extention is within physiological limit of those muscles). Thus, the heart contracts with increased (decreased) force automatically pumping the changing amount of blood into the arteries.

A result of the Frank-Sterling law of the heart is that the pumping of the heart is almost entirely independent of pressure changes in the aorta. The mean aorta pressure can increase by say 100% above the normal value without significantly reducing the output of the heart. This effect is quite important in that it permits the tissues of the body to control the cardiac output by simply increasing (decreasing) the flow of blood through them. Thus, during exercise when the muscles require increased oxygen, they allow increased blood flow and the heart automatically adjusts to the demand.

Blood flows from the large veins into the right atrium from which it passes into the right ventricle and is pumped into the pulmonary artery. The Swans Ganz catheter is used to measure cardiac output by the thermal dilution technique. The catheter is passed through a large vein, the right atrium, right ventricle, the main pulmonary artery and into a pulmonary artery branch. Quite often, the balloon associated with the Swans Ganz catheter is inflated with air to float the catheter into the position. A pressure sensor at the distal end of the catheter allows the pulmonary wedge pressure to be measured when the balloon is inflated to block the artery. (The wedge pressure measured on the pulmonary arterial side equals the pressure in the pulmonary veins which in turn is approximately equal to the pressure in the left atrium.)

The thermal dilution catheter is equipped with a fluid injectate lumen and thermistors and has its distal end placed in a branch of the pulminary artery. The thermodilution method provides a means of measuring cardiac output by injecting a cold solution into the blood stream such that it is mixed with the blood in heart. The blood in the heart is then pumped past the catheter in the pulmonary artery. The temperature of the blood in the pulmonary artery is measured with a thermistor which records the dilution curve. Cardiac output is calculated by applying equation (2 0);

$$\text{Cardiac Output} = \frac{V_1(T_B - T_1)C_1C_2}{\int T_B(t)dt} \quad (2\ 0)$$

where $V_1$ is the volume of injectate (typically 10 ml for adults and 2-5 ml for smaller subjects; $T_B$ is the blood temperature; $T_1$ is the injectate temperature. $C_1$ is the density factor which takes into account the difference in specific heats and gravity between the injectate and blood (see equation (2 1));

$$C_1 = \frac{(\text{Sp. heat})(\text{Sp. gravity})\text{ injectate}}{(\text{Sp. heat})(\text{Sp. gravity})\text{ blood}} \quad (2\ 1)$$

and $C_2$ is a derived factor which tries to account for the errors inherent in the use of a thermal indicator. The demoninator $\int T_B(t)dt$ equals the total change in blood temperature with time and is equivalent to the area under the dilution curve.

The major factors which affect the accuracy of thermodilution measurements of blood flow are:

(1) Uncertainty of injectate (saline or dextrose) temperature as it passes through the extra-vascular portion of the catheter; namely, the thermal indicator (temperature) is not confined to the blood stream, thus, some indicator is lost to catheter as it moves to the injection port; there is a difference in temperature between the injectate and catheter fluid; and there is a loss of thermal indicator to the surrounding tissue; and (2) for some systems the shape of the dilution curve is not displayed; if so, there could be serious error in measurement due to inadequate injection technique, close proximity of the thermistor to the wall of the pulmonary artery, and uneven respiration and improper placement of the thermistor in the right ventricle or too far distal in the pulmonary artery.

To overcome the disadvantages of the thermodilution technique, OPTECH proposes the measurement of differential fluid pressure inside blood vessels.

Thermal dilution measurements are generally repeated no more often than every few hours. In the interval between measurements, the cardiac output is not measured.

The simplest fiber optic approach of the present invention makes use of a single fiber optic flow sensor behind the balloon (between the balloon and the heart). In this case the arterial dimensions are not measured but instead the process involves calibrating the flow sensor by means of an initial thermal dilution measurement. Subsequently, continuous measurements of $\Delta P$ and, therefore, flow will be made. If necessary, the flow sensor may be recalibrated again by means of another thermal dilution measurement. One possible source of error will be the effect of the change in temperature on the $\Delta P$ measurement. It may be necessary to collect $\Delta P$ data prior to injecting the cold saline solution and then allowing thermal equilibrium to be reached afterward before resuming $\Delta P$ measurements. If the Fabry-Perot interferometer is employed, then the sensors also may be used to measure temperature during the thermal dilution process.

FLOW CATHETER DESIGN

Figure 11:
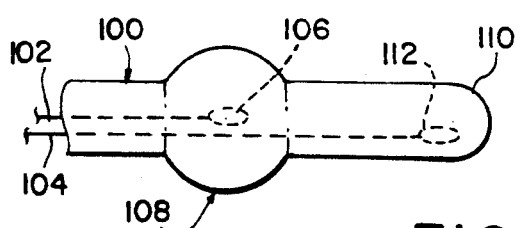
FIGS. 11–14 illustrate various fiber optic fluid flow catheter configurations.
Figure 12:
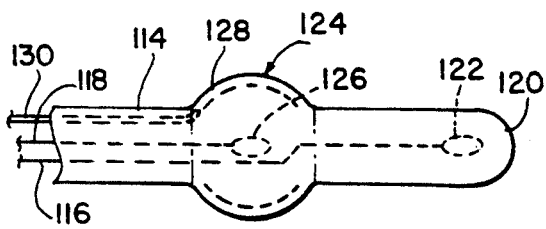
Figure 13:
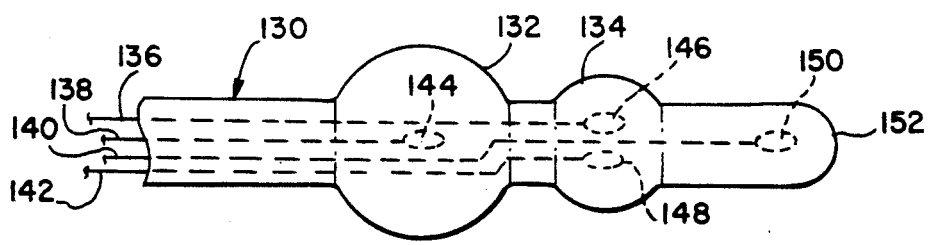
Figure 14:
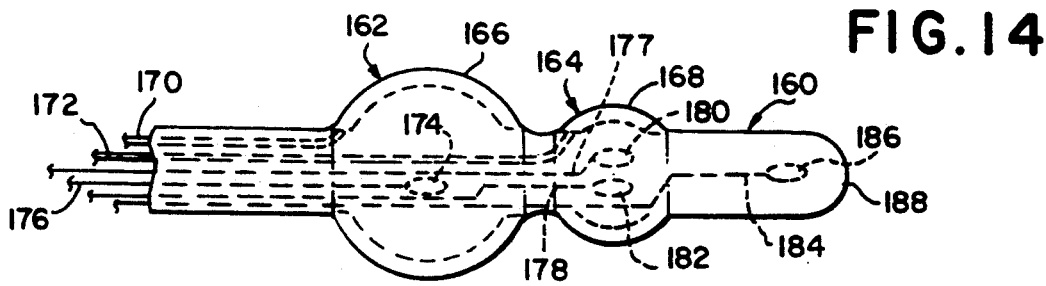

The various types of catheters depend on whether a single or multiple $\Delta P$ measurement is required and whether it is desirable to measure a taper. In FIGS. 11 and 12, examples of the flow catheter shape are shown for a single P measurement for fixed (FIG. 11) and variable (FIG. 12) enlargements. Likewise, in FIG. 13 and 14 there are shown configurations for use when two P measurements are required. Fixed and variable enlargements are shown in FIGS. 13 and 14, respectively.

Referring to FIG. 11, the probe or catheter 100 is provided with a pair of optical fibers 102 and 104. Optical fiber 102 terminates at a sensitive area 106 adjacent an enlarged zone 108. The other fiber 104 terminates near the tip end 110 in a sensitive region 112. The sensitive regions of 106 and 112 are constructed of, for example, teflon.

With respect to FIG. 12, the probe 114 is provided with a pair of optical fibers 116 and 118. Optical fiber 116 terminates near the tip end 120 in a sensitive zone 122 whereas the other fiber 118 terminates at a variable diameter region generally designated 124 at a sensitive zone 126. The variable diameter zone 124 is created by a liquid or gas filled balloon 128 and a tube 130 is employed to change the size of the balloon 128 and the tube 130 is brought to the outside via the catheter.

Where two differential pressure measurements are to be made a probe 130 (FIG. 13) is employed having two different enlarged zones 132 and 134. The system of FIG. 13 employs four optical fibers 136, 138, 140 and 142. Fiber 136 terminates in a sensitive zone 144 in the enlarged area 132. Fiber 136 terminates in the other enlarged zone 134 at a sensitive region 146. Fiber 140 also terminates in the enlarged zone 134 at sensitive zone 148 and the last fiber 142 terminates in a sensitive region 150 adjacent end 152 of the catheter.

Referring now to FIG. 14, a two differential pressure measuring catheter with variable outside shape is schematically shown at 160. The catheter 160 includes two measuring zones 162 and 164 both of which zones comprise balloons 166 and 168 respectively. The balloons 166 and 168 are connected to the catheter via conduits 170 and 172 for balloons 166 and 168 respectively. Within the zone of balloon 166 is a sensitive area 174 of optical fiber 176. Within the area of balloons 168 terminate two optical fibers 177 and 178 having sensitive zones 180 and 182. The fourth optical fiber 184 terminates at a sensitive zone 186 adjacent the end 188 of the catheter.

Pressure Sensor Fabrication

Figure 15:
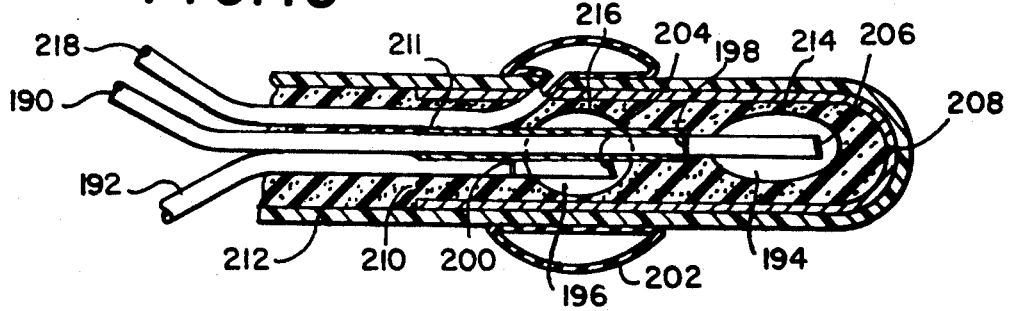
FIG. 15 illustrates a pressure measurement probe configuration for use with a Fabry-Perot interferometer.

The construction of the pressure sensitive regions depend on the type of interferometer employed. For the Fabry-Perot interferometer, the arrangement of optical fibers is shown in FIG. 15. Two fibers 190 and 192, one from each of two interferometers, are shown. The ends of each optical fiber 190, 192 have a pressure sensitive region 194 and 196 separated from the remainder of the fiber by a half-silvered mirror 198 or 200. Provision for a variable enlargment is shown in the form of a liquid-filled or air-filled balloon 202.

Each of the fibers 190 and 192 has a full mirrored end as at 204 and 206. The end portions of each of the fibers is surrounded by a rigid case 208 and the space between the inner surface of the case and the fibers is filled with silicon rubber 210. In the sensitive zone 196 of fiber 192, fiber 190 is provided with a metal jacket 211 which metal jacket protects the fiber 190 from pressure acting on the sensitive zone 196 of fiber 192. The entire catheter is formed of an outer jacket 212 of polypropylene, Teflon or other plastic which is nonthrombogenic as the outer surface is in direct contact with the blood.

Small openings as at 214 and 216 are provided in the rigid case 208 to permit pressure to be transmitted to the sensitive portions 194 and 196 of each of the fibers 190 and 192. The assembly is completed by a tube 218 which connects the balloon 202 with a source of pressure liquid or pressure gas for inflating and deflating the balloon.

Figure 16:
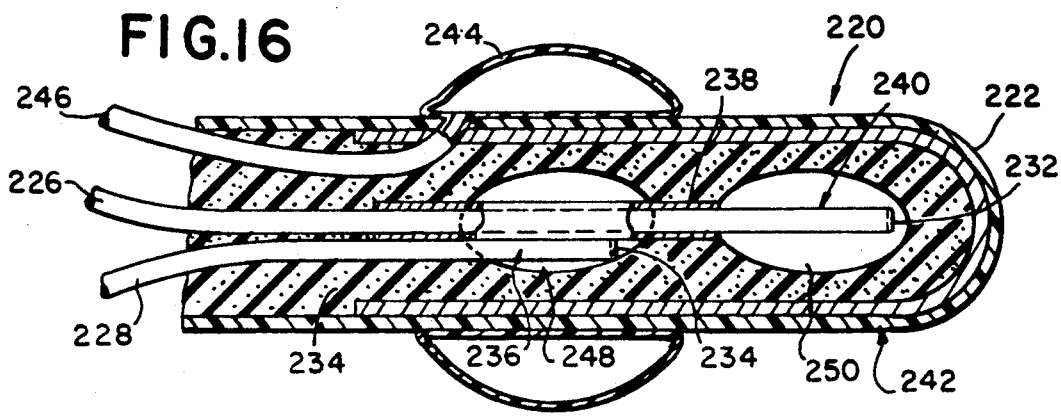
FIG. 16 is a view like FIG. 15 for use with a Michelson configured interferometer.

Referring now to FIG. 16, there is illustrated a configuration of the flow catheter for use with a Michelson interferometer. The catheter generally designated 220 comprises a polypropylene outer jacket 222, an inner hard jacket 224 and, within the hard jacket are a pair of optical fibers 226 and 228 each connected to the same interferometer (not shown in FIG. 16). Each of the fibers 226 and 228 is provided with a full-mirrored end as at 230 and 232. The area between the hard jacket and the pair of fibers is filled with silicon rubber 234. In the sensitive zone 236 of fiber 228, fiber 226 is provided with a metal jacket 238 which metal jacket protects the fiber 226 from pressure acting on the sensitive zone 236 of fiber 228. Fiber 226 has its sensitive zone 240 in the region of catheter end 242. Around the sensitive zone 236 is a balloon 244 connected to an external source of liquid or gas via tube 246. Openings 248 and 250 are provided in the hard jacket 224 to permit pressure fluid to act on the sensitive zones 240 and 236 of the two fibers.

Figure 17:
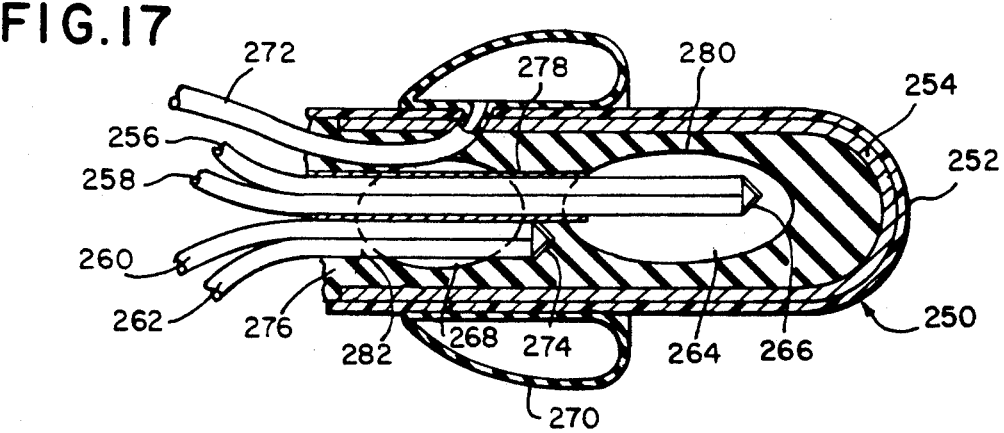
FIG. 17 is a view like FIGS. 15 and 16 of a probe associated with a Mach-Zehnder interferometer configuration.

Referring now to FIG. 17 of the drawing, a catheter 250 is illustrated for use with an interferometer of the Mach-Zehnder type. The catheter is provided with an outer polyethylene sheath 252, an inner rigid case 254, and four optical fibers 256, 258, 260 and 262 in pairs. The pair of fibers 256 and 258 extend into a sensitive zone 264, and the fibers terminate at a prism 266 so that light, for example, travelling in fiber 258 is directed into fiber 256. Similarly, fibers 260 and 262 terminate in a sensitive zone 268 surrounded by the balloon 270 which balloon is connected to liquid or compressed air via tube 272. The two fibers 260 and 262 are provided with a prism 274 which prism enables light, for example, travelling in fiber 262 to be directed into fiber 260. As in the previous forms of the invention, the space between the fibers is filled with silicon rubber 276 and the two fibers 256 and 258 passing through the sensitive zone 268 are shielded from pressure by a metal tube 278. Further, openings are provided in the rigid casing as at 280 and 282 to permit external pressure into the two sensitive zones 268 and 264. The two fibers 260 and 258 form the reference arm of the Mach-Zehnder configured interferometer and the other two fibers 256 and 260 form the measuring portion of the interferometer.

ADDITIONAL APPLICATIONS

There are a number of other applications where a small flow sensor may be used and where no existing flow technique will suffice. In the case of a stenosis (a constriction in the artery due to plaque and fatty deposits), the extent of the constriction can be determined by measuring the flow on each side of the stenosis and in the region of the stenosis. Furthermore, if an angioplastic or chemical technique is employed, then such a sensor can be used to determine the success of the procedure. In the latter case, a provision for administering the chemical to dissolve the constriction can be incorporated into the same catheter.

Figure 18:
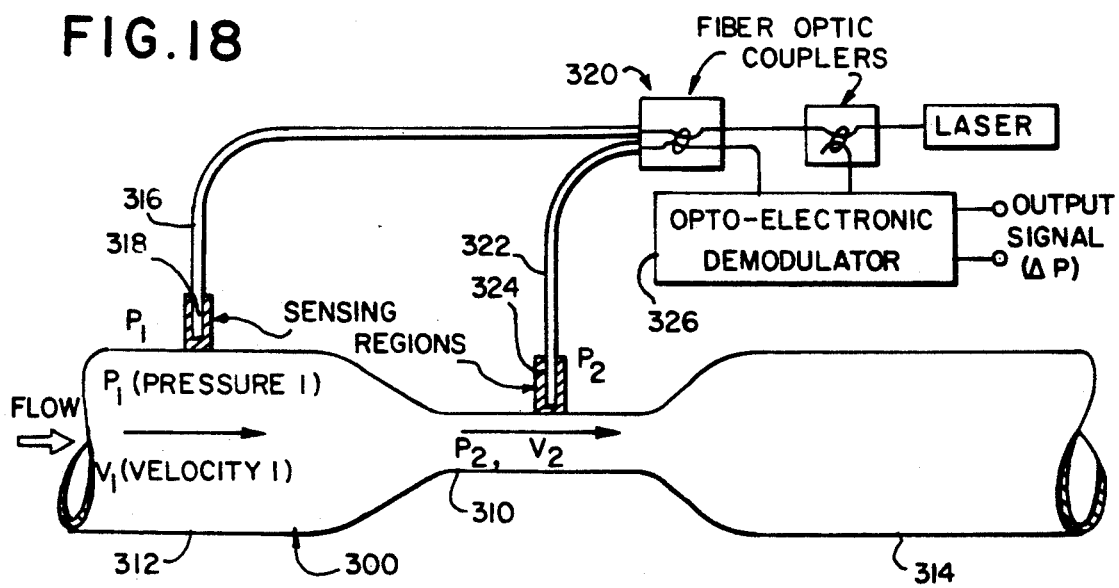
FIG. 18 illustrates diagramatically an industrial application of the present invention.

Referring now to FIG. 18 of the drawing, there is illustrated an industrial application of the fluid flow sensing apparatus employing the novel differential optical fiber pressure sensors. In FIG. 18, 300 comprises a conduit having a known area which conducts a fluid flowing in the direction of the flow arrow C. The conduit 300 has a constricted region 310 which changes the pressure/velocity relationship of the fluid in the conduit from that in sections 312 and 314. In section 312, an optical fiber 316 is mounted with its sensitive region 318 in fluid pressure transmitting relation to the fluid pressure in conduit section 312 to sense the pressure of the fluid in section 312. The optical fiber 316 is connected to one leg of a Michelson interferometer generally designated 320 configured like the Michelson interferometer hereinbefore shown and described in reference to, for example, FIG. 5 of the drawing.

In the constricted region 310, the second optical fiber 322 is mounted at its sensitive region 324 to sense the pressure of the fluid in constricted section 310. The ends of the pair of sensing fibers 316 and 322 are mirrored as in the form of the invention illustrated in FIG. 5. The output from the opto-electronic demodulator 326 represents the differential pressure in the two regions of the conduit 300.

Figure 19:
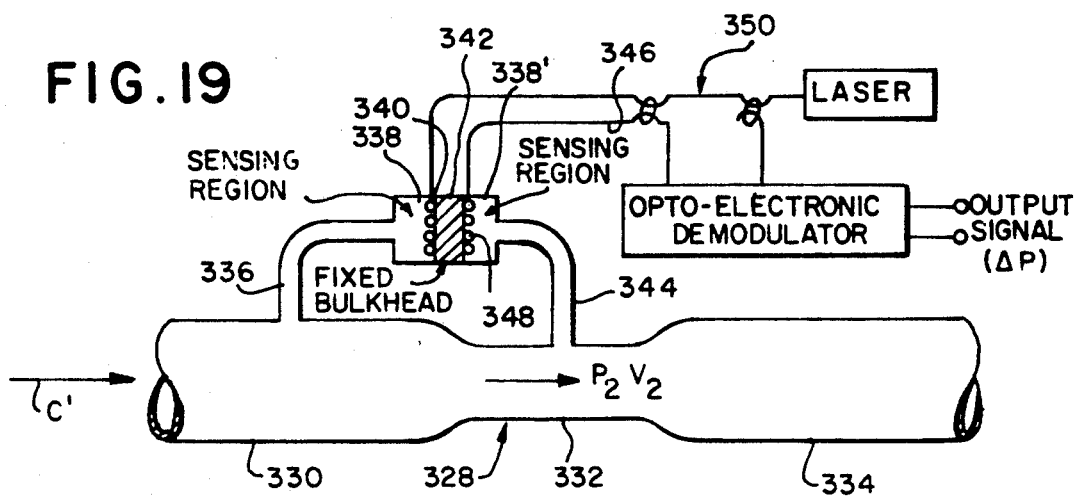
FIG. 19 is a diagramatic view of another form of the present invention useful for industrial applications.

Instead of directly coupling the sensitive ends 318 and 324 to the two pipe sections 312 and 324, the coupling to the optical fibers may be at a position remote from the conduit whose flow is being determined. Such a configuration is shown in FIG. 19 illustrating a pipe 328 having a normal crossectional area zone 330, a constricted crossectional area zone 332 and a normal crossectional area zone 334 following the constricted zone. Flow in the conduit or pipe 328 is illustrated by flow arrow C'.

In pipe section 330, a small conduit 336 is directed to a chamber or sensing region 338. In the chamber 338 is attached an optical fiber 340 at its sensitive region. The optical fiber 340 is mounted to a bulk head 342. Similarly, a tube or conduit 344 directs the fluid in the constricted section 332 to a sensing chamber 338' on the opposite side of bulk head 342. The second optical fiber 346 has its sensitive region 348 mounted to the bulk head 340. The two optical fibers 340 and 348 are connected to the two legs of a Michelson interferometer 350 in the same manner as illustrated and described in reference to FIG. 5 of the drawing, and the output from the opto-electronic demodulator is a signal $\Delta P$, the pressure differences between the fluid in sections 330 and 332 of the pipe.

Figure 20:
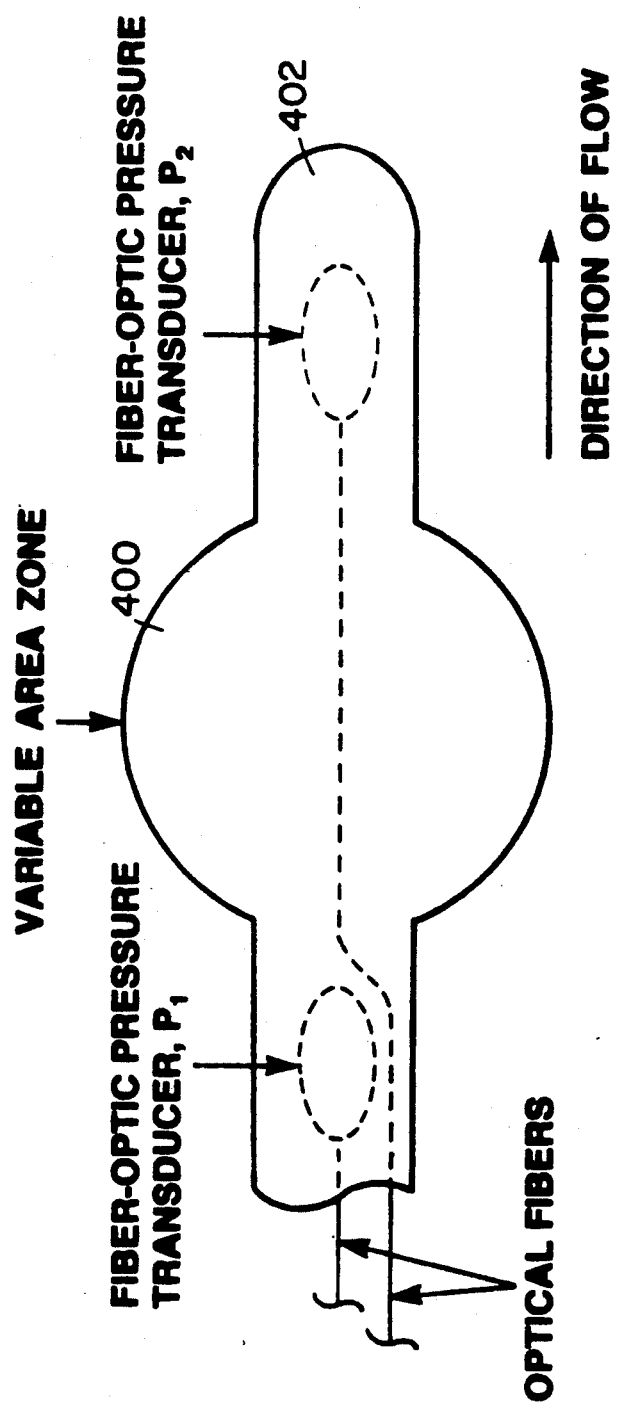
FIG. 20 is a diagramatic illustration of a modified form of fiber-optic flow catheter.

Measuring Flow by Using Fiber Optic Pressure Sensors in a Differential Producer The system of the invention also includes a differential pressure wherein the flow can be determined by placing the fiber optic transducer before and after an obstruction. This arrangement is shown in FIG. 20. The geometry of the obstruction and pressure measuring locations allow this configuration to behave in the same manner as a concentric orifice flowmeter, with the same relations applying.

Generating the differential pressure requires that the fluid must go through an abrupt change in flow area as at 400 followed by an equally abrupt return to normal or at 402. In the orifice-type flowmeters already in use, this is accomplished by forcing the flow through a small hole with sharp or slightly circular edges upstream and sharp edges downstream. The ratio of the diameter of the hole, d, to the diameter of the normal flow area, D, is called $\beta$, the beta ratio.

In this type of device the flow rate is proportional to the square root of the difference between the upstream pressure, P1, and the downstream pressure, P2. Hence, the equation of flow for this geometry is:

$$q = F\sqrt{\frac{h}{\rho f}}$$

Where:
q = flow rate
h = differential static pressure head
$\rho f$ = density of fluid F is a constant known as the Flow Coefficient. This number adjusts the flow equation for contraction characteristics, pressure measurement locations and velocity profile (Reynolds number); all of which have an effect on the accuracy of the device. The Flow Coefficient also includes an adjustment for the dimensional units used.

The formula for F is:*

$$F = \frac{Od^2}{\sqrt{1-\beta^4}} \cdot K$$

Where:
d = diameter of obstruction
$\beta = d/D$
K = adjustment for dimensional units
C = discharge coefficient

* The flow coefficient usually includes a factor for thermal expansion and gas expansion. These are neglected as they have no real effect in this situation.

All items in F are constant excepting the discharge coefficient, C. This is a dimensionless number which reflects the ratio of the true flow rate to the theoretical flow rate. C comes from the permanent loss of static pressure due to the turbulence from the device itself and is required in all flow meters of this type. It must be determined experimentally.

The diameter of the obstruction can vary from 80% to 25% of D depending on how much accuracy is desired and how much permanent head loss is acceptable. This head loss is dependent on the turbulence created (which increases as the diameter of the orifice decreases), but the sensitivity of the meter is related to the magnitude of the differential that can be induced (which also increases as the diameter decreases).

Figure 21:
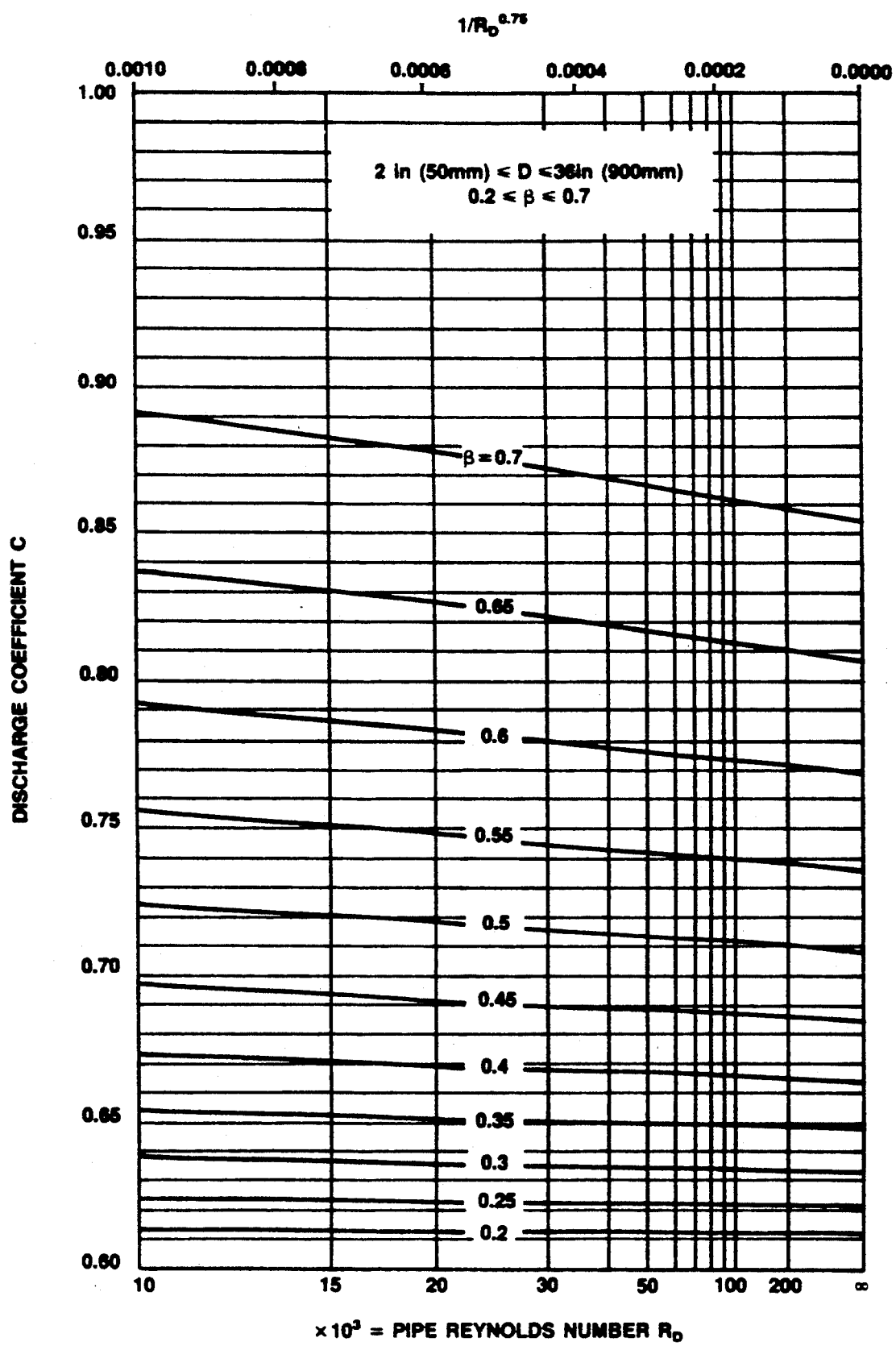
FIG. 21 is a graph showing discharge coefficient C versus the pipe Reynolds number $R_D$ for square edged orifice 2½ D and 8 D pipe taps.

Another factor influencing the design of the meter is the orifice diameter's effect on the discharge coefficient over the range of flow rates, FIG. 21 shows this coefficient plotted vs. the Reynolds number. In the ranges considered, it can be seen that while a $\beta$ of 0.7 gives less head loss than a $\beta$ of 0.2, the discharge coefficient remains much more stable at $\beta = 0.2$ than at $\beta = 0.7$.

The conclusion is that the best design for a differential producer of this type is a balance of desired linearity and acceptable head loss.

Figure 22:
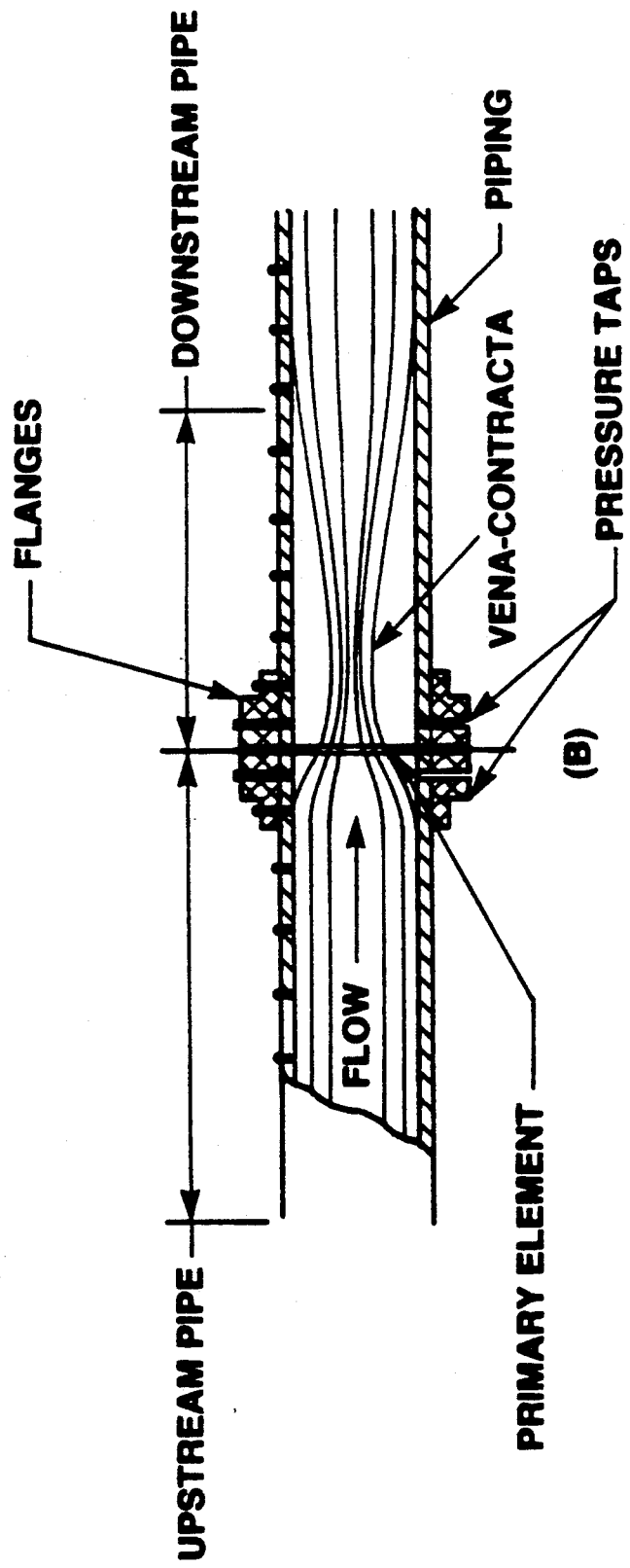
FIG. 22 illustrates elements of a differential-producer flowmeter.

It should also be noted that placement of the pressure sensing areas $P_1$ and $P_2$ in the meter also has an effect on the accuracy. The largest differential occurs between the free stream pressure taken before the obstruction and the pressure at the vena contracta—the point where the diameter of the coherent jet of fluid coming from the orifice reaches its smallest cross-sectioned area (FIG. 22). Since this is the case, measuring the pressures at any other point after the orifice will give a lower differential than is actually occurring. However, any misplacing of these taps will be accounted for in the discharge coefficient and any calibration curve that would be generated for the device.

Figure 23:
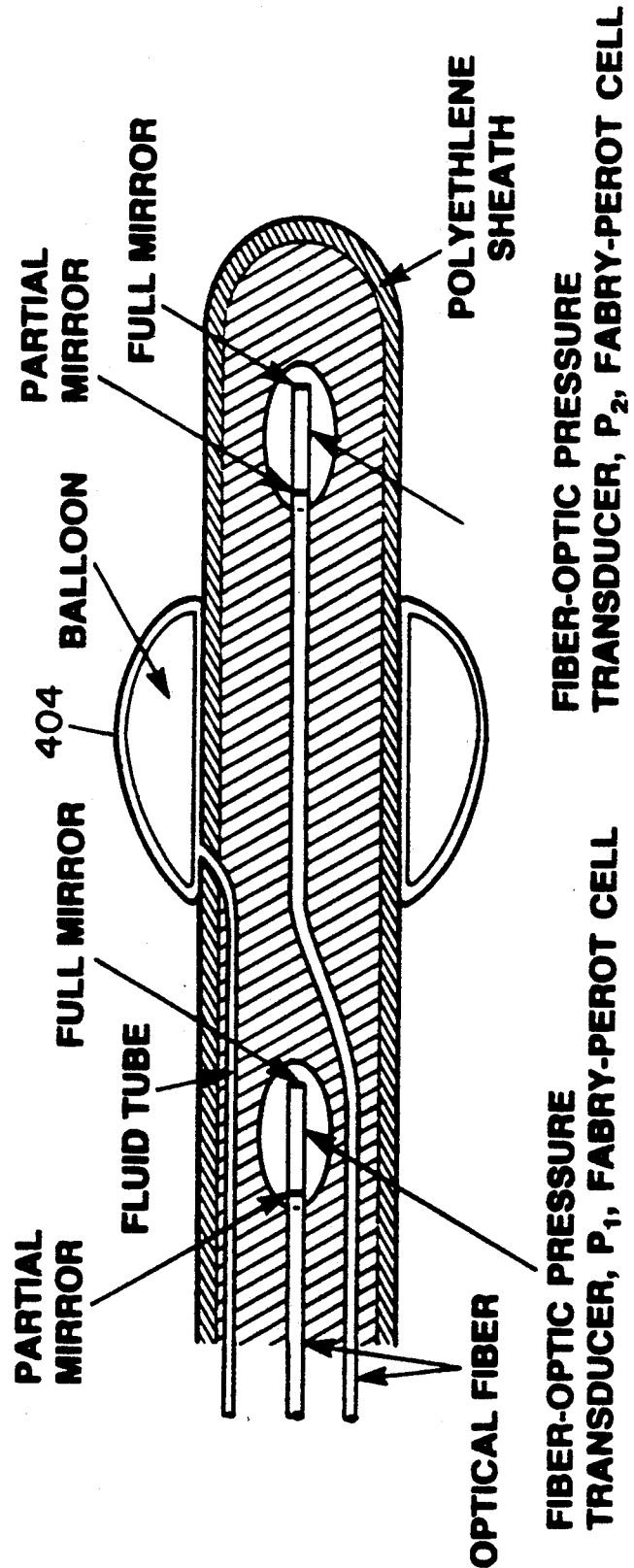
FIG. 23 diagramatically illustrates a variable constriction type fiber-optic flow catheter.

In this invention the differential pressure is produced by the variable diameter zone 404 (FIG. 23). The maximum diameter of the obstruction is in the center. The sides are rounded in such a way as to provide an abrupt change in flow area without being sharp, so as not to injure the patient. The constricted flow will travel between the edges of the zone 404 and the walls of the blood vessel, not shown. Hence, the device will behave like an orifice flowmeter, excepting that the positions of the orifice and the obstruction are reversed.

The pressures are detected by the optical fiber transducers $P_1$ and $P_2$ and are resolved by an interferometer of the Fabry-Perot type. These transducers will cover a discrete area of the catheter and provide the average pressure in that region. The flow rate is proportional to the square-root of the difference between these two pressures.

The equation for the flow rate will be:

$$q = F \cdot \sqrt{\Delta h}$$

Where:
q = flow rate in cm3/min

Δh = head differential detected in mmHg $$F = \left( \frac{Cd^2}{\sqrt{\rho f(1 - \beta^4)}} \cdot 76.89 \right) \frac{cm^3}{min\text{-}mmHg}$$

The diameter of the obstruction is dictated by the size of blood vessels being examined. FIG. 23 shows an alternative modification to the catheter-probe in which the obstruction consists of an expandable sac 404 that is inflated with fluid or air when a measurement is being taken and deflated when not in use. This feature allows for: (1) prolonged exposure to the patient with little effect on circulation (while in its deflated state); (2) the ability to adjust to different diameter blood vessels in the body; and (3) maximum pressure differential while at the same time feeding back the diameter of the obstruction for flow calculation.

The diameter of this sac 404 is determined by measuring the amount of fluid needed to inflate it. Since the radius of the sphere will vary with the cubed-root of its volume, the amount of fluid injected will give the change in radius of the obstruction.

Using Fiber Optic Differential Pressure Measurement To Detect Arterial Blockages (Stenosis)

Figure 24:
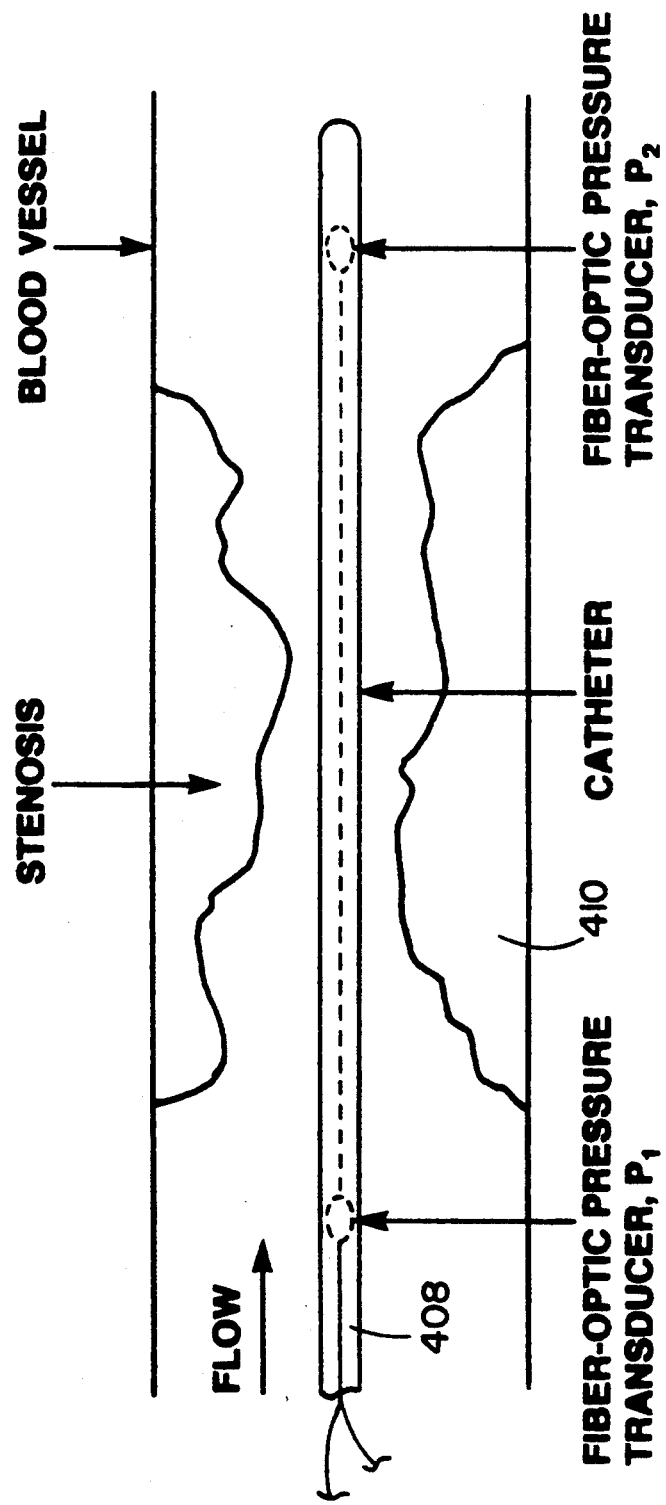
FIG. 24 diagramatically illustrates a fiber-optic catheter designed to measure blood flow past a stenosis.

The invention also takes the form of a straight catheter 408 with no obstructions to the blood vessel and 2 fiber optic pressure transducers $P_1$ and $P_2$ placed some distance apart along the catheter's length (FIG. 24). By traversing the blood vessel and monitoring the two pressures, an abrupt narrowing in the vessel of finite length (stenosis) 410 is detected by observing a difference in the two pressures.

The cause of the pressure differential will be the increase in velocity of the fluid while in, and immediately after the blockage by the Bernoulli effect and the permanent pressure loss due to turbulence in the flow from the stenosis.

By the flow (Bernoulli) equation, the pressure drop between the free-stream flows and the minimum flow area of the stenosis is:

$$\Delta h = 1.3 \times 10^{-2} \cdot q \cdot \rho f \frac{[1 - (d/D)^4]}{d^4}$$

Where:

Δh = head loss between free stream flow and stenosis flow in mmHg
q = flow rate in cm3/min
$\rho f$ = fluid density in gr/cm3 d = diameter of flow area through stenosis in cm
D = normal diameter of blood vessel The diameter of the obstruction can be determined by solving for d:

$$d = \frac{x}{1 + (X/D^4)}$$

Where:

$$x = \frac{1.3 \times 10^{-2} \cdot q^2 \rho f}{\Delta h}.$$

I claim:

1. A fiber optic fluid pressure measuring device comprising a first optical fiber configured as a Fabry-Perot interferometer, a pressure responsive end on the first optical fiber, said pressure responsive end of said optical fiber including a first partial mirror and a mirrored end spaced therefrom, means positioning said responsive end in the fluid to be measured, a second optical fiber configured as a second Fabry-Perot interferometer, a pressure responsive end, said pressure responsive end of said second optical fiber including a first partial mirror and a mirrored end spaced therefrom, a constriction in the fluid to be measured spaced from the means positioning the first responsive end in the fluid to be measured, means positioning the second optical fiber responsive end in the fluid at the other side of the constriction, radiant energy emitting means for directing radiant energy to the interferometers and through their optical fiber responsive ends, and radiant energy detecting means connected to said interferometers.

2. Means for measuring fluid flow in arteries and veins comprising a catheter, fiber optic differential pressure measuring means housed in the catheter, said pressure measuring means comprising a first optical fiber configured as a first Fabry-Perot interferometer, a first fluid pressure responsive end on the first optical fiber, means mounting the first optical fiber responsive end in one end of the catheter, an enlarged zone formed on the catheter spaced from the first responsive end, a second optical fiber configured as a second Fabry-Perot interferometer, a second fluid pressure responsive end on the second optical fiber, means mounting the second pressure responsive end on the other side of said enlarged zone from the first responsive end, each of the optical fiber responsive ends including a first partial mirror and a mirrored end spaced therefrom, radiant energy emitting means for directing radiant energy to the interferometers, and through said first and second responsive ends, and radiant energy detecting means connected to said first and second interferometers.

* * * * *